(12) United States Patent
Becke et al.

(10) Patent No.: US 6,570,031 B1
(45) Date of Patent: May 27, 2003

(54) DENDRIMER COMPOUNDS, METHOD FOR THE PRODUCTION THEREOF, USE THEREOF AS CATALYSTS

(75) Inventors: Sigurd Becke, Rösrath (DE); Uwe Denninger, Bergisch Gladbach (DE); Michael Mager, Leverkusen (DE); Heike Windisch, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/646,839

(22) PCT Filed: Mar. 11, 1999

(86) PCT No.: PCT/EP99/01558

§ 371 (c)(1),
(2), (4) Date: Sep. 22, 2000

(87) PCT Pub. No.: WO99/48898

PCT Pub. Date: Sep. 30, 1999

(30) Foreign Application Priority Data

Mar. 24, 1998 (DE) .......................................... 198 12 881

(51) Int. Cl.[7] .............................. C07F 7/08; C07F 7/22
(52) U.S. Cl. ........................... 556/87; 556/88; 556/402; 556/431; 556/435
(58) Field of Search ........................... 556/87, 88, 402, 556/431, 435

(56) References Cited

U.S. PATENT DOCUMENTS

| | | | |
|---|---|---|---|
| 4,871,705 A | 10/1989 | Hoel | |
| 4,892,851 A | 1/1990 | Ewen et al. | |
| 5,026,798 A | 6/1991 | Canich | |
| 5,145,819 A | 9/1992 | Winter et al. | |
| 5,229,478 A | 7/1993 | Floyd et al. | |
| 5,276,208 A | 1/1994 | Winter et al. | |
| 5,334,677 A | 8/1994 | Razavi et al. | |
| 5,565,534 A | 10/1996 | Aulbach et al. | |
| 5,703,187 A | 12/1997 | Timmers | |
| 5,710,297 A | 1/1998 | Weller et al. | |
| 5,986,029 A | 11/1999 | van Beek et al. | |
| 5,990,254 A | 11/1999 | Weller et al. | |
| 6,013,819 A | 1/2000 | Stevens et al. | |
| 6,075,077 A | 6/2000 | Timmers et al. | |

FOREIGN PATENT DOCUMENTS

| | | |
|---|---|---|
| DE | 19 516 200 | 11/1996 |
| EP | 0 277 003 | 8/1988 |
| EP | 0 277 004 | 8/1988 |
| EP | 0 129 368 | 7/1989 |
| EP | 0 468 537 | 11/1996 |
| EP | 0 561 479 | 11/1996 |
| EP | 743 313 | 11/1996 |
| WO | 93/11172 | 6/1993 |
| WO | 97/01565 | 1/1997 |
| WO | 97/32908 | 9/1997 |

OTHER PUBLICATIONS

J. Am. Chem. Soc. (month unavailable) 1991, 113, pp. 3623–3625, Yang et al "Cation–like", Homogenerous Olefin polymerization Catalysts Based upon Zirconocene Alkyls and Tris(pentafluorophenyl) borane.

J. Org. Chem (month unavailable) 1990, 55, pp. 2274–2275, Soundararajan et al, Hydroboration with Boron Halides and Trialkylsilanes.

Rubber Chem. Technol. (month unavailable) 1992, pp. 303–314, Zhout et al, Synthesis and Properties of Regular Star Polybutadienes with 32 Arms.

Adv. Mater. (month unavailable) 1993, 5, No. 6, pp. 466–468, van der Made et al, Dendrimeric Silanes.

Marcromolecules (month unavailable) 1993, 26, pp. 963–968, Zhou et al, Synthesis of Novel Carbosilane Dendritic Macromolecules.

J. Chem. Soc., Chem. Commun., (month unavailable) 1994, Alonso et al, Organometallic Silicon Dendrimers.

Organometallics (month unavailable) 1994, 13, pp. 2682–2690, Seyferth et al, Synthesis of an Organosilicon Dendrimer Containing 324 Si–H Bonds.

Macromolecules (month unavailable) 1995, 28, pp. 6657–6661, Lorenz et al, Carbosilane–Based Dendritic Polyols.

Organometallics, (month unavailable), 1995, 14, pp. 5362–5366, Seyferth et al, Preparation Of Carbosilane Dendrimers with Peripheral Acetylenedicobalt Hexacarbonyl Substituents.

Primary Examiner—Paul F. Shaver
(74) Attorney, Agent, or Firm—Joseph C. Gil; Noland J. Cheung; Jennifer R. Seng

(57) ABSTRACT

The present invention relates to a novel dendrimic compounds, to a method for the production thereof and to the use thereof as catalysts for the production of polymers, in particular to the use thereof as co-catalysts for metallocenes for polymerizing unsaturated compounds.

2 Claims, No Drawings

DENDRIMER COMPOUNDS, METHOD FOR THE PRODUCTION THEREOF, USE THEREOF AS CATALYSTS

FIELD OF THE INVENTION

The present invention relates to novel dendrimeric compounds, to a method for the production thereof and to the use thereof as catalysts for the production of polymers, in particular to the use thereof as co-catalysts for metallocenes for polymerizing unsaturated compounds.

BACKGROUND OF THE INVENTION

It has long been known to use metallocenes in combination with activating co-catalysts, preferably alumoxanes (MAOs), for polymerising olefins and diolefins (c.f. for example EP-A 129 368, 347 128, 347 129, 351 392, 485 821, 485 823).

However, catalyst systems based on metallocenes and alumoxanes have considerable disadvantages. Thus alumoxanes, in particular MAOs, cannot be produced with a high degree of reproducibility either in situ or in a pre-forming process. MAO is a mixture of various species containing aluminum which exist in equilibrium with each other, resulting in a loss of reproducibility during the polymerization of olefinic compounds. Moreover, MAO is not stable in storage and the composition thereof changes on exposure to extreme temperatures. Another serious disadvantage is the considerable excess of MAO which is necessary for the activation of metallocenes. However, this high MAO/metallocene ratio is an absolute prerequisite for achieving high catalyst activities. This results in a crucial processing disadvantage, however, since aluminum compounds must be separated from the polymers during work-up. Furthermore, MAO is a cost-determining factor in the use of catalyst systems containing MAO, meaning that excesses of MAO are uneconomic.

In J. Am. Chem. Soc. 1991, 113, 3623, tris (pentafluorophenyl)borane is described as a co-catalyst for metallocene dialkyls. However, the polymerisation activity of catalysts based on tris(pentafluorophenyl)borane is unsatisfactory. EP-A 277 003 and 277 004 describe ionic catalyst systems which are produced by the reaction of metallocenes with ionizing reagents. Perfluorinated, tetraaromatic borate compounds, in particular tetrakis(pentafluorophenyl)borate compounds, are used as ionizing reagents (EP 468 537, EP 561 479). However, the production and introduction of pentafluorophenyl substituents is complex and costly. Using tetrakis(pentafluorophenyl)borate compounds on an industrial scale is thus highly cost-intensive. Another disadvantage of tetrakis(pentafluorophenyl)borate compounds is the poor solubility thereof in hydrocarbons.

WO 93/11172 describes polyanionic activators for metallocenes which consist, for example, of a polystyrene matrix onto which what are termed non-coordinating anions, preferably borate compounds comprising pentafluorophenyl substituents, are chemically bonded. The catalytic activity of the borate compounds described above decreases considerably, however, if the fluoroaromatic substituents on the boron are replaced by other substituents, for example by methyl or butyl substituents.

In comparison with the activators described in EP 468 537, for example N,N-dimethylaniliniumtetrakis (pentafluorophenyl)borate, the polyanionic activators (God described in WO 93/11172 exhibit lower polymerization activity. Another disadvantage is the poor yield during the production of the polyanionic activators. Costly tris (pentafluorophenyl)borane is used as a starting compound which must be chemically bonded by a complicated method onto a matrix, for example crosslinked polystyrene. The polyanionic activators do not have a uniform surface, wherein accessibility of the molecular surface or the active end groups may be restricted. The precise composition, in particular the number of active end groups of the polyanionic activators is not known. The polyanionic activators have neither a defined molecular size nor dimensional stability. The poor meterability of polyanionic activators is industrially disadvantageous. The sparingly soluble polyanionic activators are used as solids for catalysing polymerization, which is technically disadvantageous in a continuous polymerization process.

SUMMARY OF THE INVENTION

The object thus arose of identifying novel co-catalysts which avoid the above-stated disadvantages. In particular, the object consisted in creating a cost-effective catalyst system which is easy to produce, easy to handle industrially and is capable of polymerizing unsaturated compounds, such as for example olefins and dienes, at a high level of catalytic activity.

It has surprisingly now been found that dendrimeric compounds which contain metals, preferably in combination with metallocenes, are particularly suitable for achieving the above-stated objects.

The present invention accordingly provides novel dendrimeric compounds of the general formula

in which
  X represents $Me^2R^2R^3(R^y)_r$,
  $R^1, R^2, R^3, R^y$ are identical or different, may optionally be mono- or polysubstituted and represent hydrogen, $C_5$–$C_{20}$ cycloalkyl, $C_1$–$C_{20}$ alkyl, $C_7$–$C_{40}$ aralkyl, $C_6$–$C_{40}$ aryl, $C_1$–$C_{10}$ alkoxy, $C_6$–$C_{40}$ aryloxy, silyloxy or halogen,
  $R^4$ represents an optionally mono- or polysubstituted alkylene, alkenylene or alkynylene residue, which is optionally interrupted by one or more heteroatoms.
  $Me^1$ represents an element of group IVa of the periodic system of the elements (IUPAC nomenclature),
  $Me^2$ represents an element of group IIIa of the periodic system of the elements (IUPAC nomenclature),
  i represents an integer from 2 to 4,
  n represents an integer from 1 to 20 and
  r represents 0 or 1
    wherein, when r=1, the $Me^2$ residue bears a negative formal charge and in the event of a negative formal charge on $Me^2$, this is offset by a cation,
or in which
  X represents $Me^1R^5{}_a[(R^4)_mMe^2R^2R^3(R^y)_r]_{3-a}$,
  $Me^1, Me^2, R^1, R^2, R^3, R^4, R^y$, i, n, r have the above-stated meanings,
  $R^5$ has the meaning of the residues $R^1, R^2, R^3, R^y$,
  m is identical to or different from n and represents integers from 1 to 20 and
  a represents 0, 1 or 2,
or in which
  X represents $Me^1R^5{}_a[(R^4)_mMe^1R^6{}_b[(R^4)_pMe^2R^2R^3 (R^y)_r]_{3-b}]_{3-a}$, Me$^1$, Me$^2$, R$^2$, R$^3$, R$_4$, R$^y$, i, n, r, m, a have the above-stated meanings, R$^6$ has the meaning of the residues R$^1$, R$^2$, R$^3$, R$^y$, R$^5$, b represents 0, 1 or 2 and p represents integers from 1 to 20, wherein the compounds described in DE 195 16 200 are excluded, said compounds being produced by the reaction of silicon tetrachloride in a Grignard reaction to form tetraallylsilane, which is subsequently reacted twice or more alternately
a) with trichlorosilane in a quantitative reaction in the presence of a catalyst and then
b) with an allyl compound in a Grignard reaction using a suitable solvent in each case until a dendrimeric skeleton comprising outwardly pointing allyl groups is obtained, the outer allyl groups of which
c) are derivatized in a hydroboration reaction with 9-borabicyclo[3.3.1]nonane.

DETAILED DESCRIPTION OF THE INVENTION

Suitable cations in the event that Me$^2$ bears a negative formal charge which may be considered are ions of atoms or molecules such as alkali metal ions, for example Li$^+$, Na$^+$ or K$^+$, alkaline earth metal ions such as Be$^{2+}$, Mg$^{2+}$, Ca$^{2+}$, Ba$^{2+}$, transition metal ions such as Zn$^{2+}$, Cd$^{2+}$, Mg$^{2+}$, Cu$^+$, Cu$^{2+}$, or organic compounds such as ammonium or phosphonium ions of the NR$_4^+$ or PR$_4^+$ type, preferably Ph—N(CH$_3$)$_2$H$^+$, or carbocations of the CR$_3^+$ type, preferably CPh$_3^+$.

The nature of the cation NR$_4^+$ in particular also has an influence on the solubility of the salts, consisting of the dendrimeric compounds according to the invention of the formula (I) which have at least one negative formal charge (r=1) and cations which offset the formal charge. The solubility of the stated salts in non-polar solvents, such as for example toluene and xylene, may, for example, be improved by using ammonium salts NR'R$_3^+$ which contain a relatively long-chain, branched or unbranched hydrocarbon residue R'. R' is here preferably an unbranched C$_6$–C$_{40}$ alkyl residue, particularly preferably a C$_8$–C$_{12}$ alkyl residue. The remaining residues R in NR$_3$R' may, mutually independently, be hydrogen and optionally mono- or polysubstituted C$_1$–C$_5$ alkyl and C$_6$–C$_{12}$ aryl residues. At least one residue R in NR$_3$R' is preferably hydrogen. Specifically, cations such as undecyldimethylammonium and dodecyldimethylammonium may be mentioned.

Cycloalkyl residues in the formula (I) which may in particular be considered are those having 5 to 10 carbon atoms. Example which may be mentioned are cyclopentyl, cyclohexyl, cycloheptyl or cyclooctyl residues, fused cycloaliphatic residues such as decalin or hydrindene residues or bicyclic residues such as norbornyl residues.

Cyclopentyl, cyclohexyl and norbornyl residues are preferred.

Preferred alkyl residues are those having 1to 10 carbon atoms, the following being mentioned by way of example: methyl, ethyl, propyl, n-butyl, pentyl, hexyl, heptyl, octyl, isopropyl, sec.-butyl, tert.-butyl or neopentyl, preferably methyl, ethyl, propyl, n-butyl, sec.-butyl, tert.-butyl.

Aralkyl residues which may be mentioned are those having 7 to 20 carbon atoms, preferably the benzyl residue.

Preferred aryl residues which may be considered are those having 6 to 20 carbon atoms, the following being mentioned by way of example: phenyl, toluyl, p-halophenyl, mesityl, pentafluorophenyl, bis(3,5-trifluoromethyl)phenyl, more preferably pentafluorophenyl, bis(3,5-trifluoromethyl)phenyl, most preferably pentafluorophenyl.

Aryloxy residues which may in particular be considered are those having 6 to 10 carbon atoms, phenyloxy residues being mentioned by way of example.

Silyloxy residues which may be considered are compounds of the type —O—SiR$_3$, in which R denotes C$_1$–C$_{10}$ alkyl residues or C$_6$–C$_{10}$ aryl residues. Silyloxy residues, such as —O—SiMe$_3$, —O—SiEt$_3$ and —O—SiPh$_3$, are preferred.

Examples of halogens which are used are fluorine, chlorine and bromine, in particular fluorine and chlorine.

As mentioned above, depending upon the number of C atoms, the residues R$^1$, R$^2$, R$^3$, R$^4$ and R$^y$ of the formula (I) may be mono- or polysubstituted, preferably mono- to decasubstituted, particularly preferably mono- to pentasubstituted. Substituents which may be considered are, for example, the above-mentioned cycloalkyl, alkyl, aralkyl, aryl, alkoxy, aryloxy and silyloxy residues, as well as the stated halogens. Preferred substituents are halogens, in particular fluorine, alkyls, such as methyl and ethyl, perhalogenated alkyls, such as CF$_3$, or perhalogenated aromatics, such as C$_6$F$_5$.

Elements of main group 4 of the periodic system of elements which may be mentioned are Si, Ge, Sn and Pb, preferably Si, Ge, Sn, in particular Si.

Elements of main group 3 of the periodic system of elements which may be considered are B, Al, In and Ga, preferably B, Al, very particularly preferably B.

In the formula (I), i preferably represents the numbers 3 or 4, particularly preferably 4, n is an integer from 1 to 10, in particular 2 to 5, and r represents 0.

In the formula (I), m furthermore preferably represents integers from 1to 10, in particular from 2 to 5, a represents 0, b represents 0 and p represents integers from 1 to 10, in particular 2 to 5.

Dendrimeric compounds which may be considered are preferably those of the formula (II)

in which

X represents Me$^2$R$^2$R$^3$(R$^y$)$_r$, and R$^1$, R$^2$, R$^3$, R$^y$ are identical or different, preferably identical, may optionally be mono- or polysubstitluted, and represent C$_5$–C$_6$ Cycloalkyl, C$_6$–C$_{10}$ aryl, C$_1$–C$_{10}$ alkyl and/or halogen, R$^4$ represents a methylene residue, Me$^2$ represents boron or Al, i represents an integer from 2 to 4, n represents an integer from 1 to 20, r may be 0 or 1, or in which X represents SiR$^5_a$[(R$^4$)$_m$Me$^2$R$^2$R$^3$(R$^y$)$_r$]$_{3-a}$, R$^5$ has the meaning of the residues R$^1$, R$^2$, R$^3$, R$^y$, m is identical to or different from n and represents integers from 1 to 20, a represents 0, 1 or 2, and Me$^2$, R$^2$, R$^3$, R$^4$, i, n, r have the above-stated meanings, or in which X represents SiR$^5_a$[(R$^4$)$_m$SiR$^6_b$[(R$^4$)$_p$Me$^2$R$^2$R$^3$(R$^y$)$_r$]$_{3-b}$]$_{3-a}$, Me$^2$, R$^2$, R$^3$, R$^4$, R$^5$, R$^y$, i, n, r, m, a have the above-stated meanings, and $R^6$ has the meaning of the residues $R^1$, $R^2$, $R^3$, $R^5$, $R^y$, b represents 0, 1 or 2 and p represents integers from 1 to 20.

Particularly preferred dendrimeric compounds are those of the general formula (III)

$$R^1{}_{4-i}Si[(CH_2)_nX]_i \qquad (III),$$

in Which

X represents $BR^2R^3(R^y)_r$ and $R^1$, $R^2$, $R^3$, $R^y$ are identical or different, preferably identical, may optionally be mono- or polysubstituted and represent $C_6$–$C_{10}$ aryl or $C_1$–$C_{10}$ alkyl, i represents 3 or 4, n represents 1 to 20 and r represents 0 or 1 or in which

X represents $SiR^5{}_a[(CH_2)_mBR^2R^3(R^y)_r]_{3-a}$, $R^5$ has the meaning of the residues $R^1$, $R^2$, $R^3$, $R^y$, m is identical to or different from n and represents integers from 1 to 20, a represents 0, 1 or 2 and $R^2$, $R^3$, $R^5$, $R^y$, i, n, r have the above-stated meanings, or in which X represents $SiR^5{}_a[(CH_2)_mSiR^6{}_b[(CH_2)_pBR^2R^3(R^y)_r]_{3-b}]_{3-a}$, $R^2$, $R^3$, $R^5$, $R^y$, i, n, r, m, a have the above-stated meanings, $R^6$ has the meaning of the residues $R^1$, $R^2$, $R^3$, $R^y$, b represents 0, 1 or 2 and p represents integers from 1 to 20.

Emphasis should be placed upon the dendrimeric compounds of the following formulae:

$Si[(CH_2)_3BCl_2]_4$ $Si[(CH_2)_3BMe_2]_4$ $Si[(CH_2)_3B(C_6F_5)_2]_4$ $Si[(CH_2)_3BMes_2]_4$ $Si[(CH_2)_3B(C_6H_3(CF_3)_2)_2]_4$ $Si[(CH_2)_3BMe_3]_4{}^{4-}4K^+$ $Si[(CH_2)_3B(n-Bu)_3]_4{}^{4-}4K^+$ $Si[(CH_2)_3B(n-Bu)_2]_4$ $Si[(CH_2)_3B(C_6F_5)_3]_4{}^{4-}4K^+$ $Si[(CH_2)_3B(C_6H_3(CF_3)_2)_3]_4{}^{4-}4K^+$ $Si\{(CH_2)_2Si[(CH_2)_3BCl_2]_3\}_4$ $Si\{(CH_2)_2Si[(CH_2)_3BMe_2]_3\}_4$ $Si\{(CH_2)_2Si[(CH_2)_3B(n-Bu)2]_3\}_4$ $Si\{(CH_2)_2Si[(CH_2)_3B(C_6F_5)_2]_3\}_4$ $Si\{(CH_2)_2Si[(CH_2)_3BMe_3]_3\}_4{}^{12-}12K^+$ $Si\{(CH_2)_2Si[(CH_2)_3B(n-Bu)_3]_3\}_4{}^{12-}12K^+$ $Si\{(CH_2)_2Si[(CH_2)_3B(C_6F_5)_3]_3\}_4{}^{12-}12K^+$ $Si\{(CH_2)_2Si[(CH_2)_3B(3,5-(CF_3)_2C_6H_3)_3]_3\}_4{}^{12-}12K^+$ $Si\{(O—CH_2)_3Si(CH_3)[(CH_2)_3BCl_2]_2\}_4$ $Si\{(O—CH_2)_3Si(CH_3)[(CH_2)_3BMe_2]_2\}_4$ $Si\{(O—CH_2)_3Si(CH_3)[(CH_2)_3B(n-Bu)_2]_2\}_4$ $Si\{(O—CH_2)_3Si(CH_3)[(CH_2)_3B(C_6H_5)_2]_2\}_4$ $Si\{(O—CH_2)_3Si(CH_3)[(CH_2)_3B(C_6F_5)_2]_2\}_4$ $Si\{(O—CH_2)_3Si(CH_3)[(CH_2)_3BMe_3]_4{}^{4-}4K^+$ $Si\{(O—CH_2)_3Si(CH_3)[(CH_2)_3B(C_6H_5)_3]_4{}^{4-}4K^+$ $Si\{(O—CH_2)_3Si(CH_3)[(CH_2)_3B(C_6F_5)_3]_4{}^{4-}4K^+$ wherein Mes represents 2,4,6-mesityl and K means a cation bearing one or more charges.

K preferably represents alkali metal ions, such as for example $Li^+$, $Na^+$, $K^+$ or carbenium ions, such as for example the triphenylmethyl cation or di- or trisubstituted ammonium ions, such as for example N,N-dimethylanilinium, trimethylammonium, triethylammonium, tri(n-butyl)ammonium, dimethylundecylammonium, dimethyldodecylammonium, dimethyloctadecylammonium, methyldioctadecylammonium, methyloctadecylammonium or dioctadecylammonium ions.

The present invention also provides a method for the production of dendrimeric compounds of the general formula (I), which method is characterized in that compounds of the general formula (IV)

$$R^1{}_{4-i}Me^1[(R^7)_{n-2}Y]_i \qquad (IV)$$

in which

Y represents $CR^8=CR^9R^{10}$, $R^8$, $R^9$ and $R^{10}$ are identical or different and represent hydrogen, alkyl, aryl or halogen, $R^7$ has the meaning of residue $R^4$ in the formula (I) and n represents an integer from 2 to 20, $R^1$, $Me^1$ and i have the definition stated for the formula (I), or in which Y represents $Me^1R^5{}_a[(R^7)_{m-2}(CR^8=CR^9R^{10})]_{3-a}$, $R^5$ has the definition stated in the formula (I), or in which Y represents $Me^1R^5{}_a[(R^4)_mMe^1R^6{}_b[(R^7)_{p-2}(CR^8=CR^9R^{10})]_{3-b}]_{3-a}$, $R^6$ has the definition stated in formula (I), m, p represent an integer from 2 to 20 and in which all the other residues stated in the formulae have the above-stated meanings for Y, are reacted with compounds of the general formula (V)

$$R^{11}Me^2R^2R^3 \qquad (V),$$

in which $R^{11}$ represents hydrogen or $C_1$–$C_{30}$ alkyl and $Me^2$, $R^2$ and $R^3$ have the meanings stated in the formula (I), and, in the event that r=1, the resultant product is further reacted with compounds of the general formula (VI)

$$Me^3—R^y \qquad (VI),$$

in which $Me^3$ represents an alkali metal and $R^y$ has the meaning stated in the formula (I), or with compounds of the general formula (VII)

$$Hal_q—Me^4—R^y{}_{2-q} \qquad (VII),$$

in which $Me^4$ represents an alkaline earth metal or transition metal of subgroups 1 or 2, Hal represents halogen, q represents 0 or 1 and $R^y$ has the meaning as before.

The preferred alkaline earth metal is Mg, with the preferred transition metals being Zn, Cd, Hg or Cu. Preferred alkali metals are Li, Na and K, particularly preferably Li.

Hydrogen and $C_1$–$C_5$ alkyl are preferred as residues $R^8$, $R^9$ and $R^{10}$, with hydrogen being particularly preferred.

The influence of the metal atom $Me^1$ in unsaturated compounds of the formula (IV) in which n, m or p=2 often results, during addition of compounds of the formula (V), in the formation of branched compounds having the following structural element

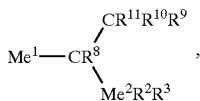

as a result of which compounds of the formula (I) in which n, m or p=1 may be obtained.

Compounds of the formulae (IV), (V), (VI) and (VII) which are preferably used are respectively those of the general formulae (IVa), (Va), (VIa) and (VIIa) shown below:

$$R^1{}_{4-i}Si[(CH_2)_nY]_i \qquad (IVa)$$

in which
Y represents —CH=$CH_2$,
i represents 3 or 4,
$R^1$ represents an optionally mono- or polysubstituted $C_1$–$C_6$ alkyl or $C_6$–$C_{12}$ aryl residue and
n represents an integer from 1 to 10,
or in which
Y represents $SiR^5{}_a[(CH_2)_m(CH=CH_2)]_{3-a}$,
a represents 0, 1 or 2 and
$R^5$ has the meaning of $R^1$,
m represents an integer from 1 to 10,
or in which
Y represents $SiR^5{}_a[(CH_2)_mSiR^6{}_b[(CH_2)_pCH=CH_2]_{3-b}]_{3-a}$,
$R^6$ has the meaning of $R^1$ and
p and m represent an integer from 1 to 10;

$$H—BR^2R^3 \qquad (Va),$$

in which
$R^2$ $R^3$ have the meaning stated in the formula (I);

$$Me^3—R^y \qquad (VIa),$$

in which
$Me^3$ represents Li or Na and
$R^y$ has the meaning stated in the formula (I);

$$Hal_q—Mg—R^y{}_{2-q} \qquad (VIIa),$$

in which
Hal represents Cl or Br and
$R^y$ has the meaning as in formula (I) and
q represents 0 or 1.

Compounds of the formula (IV) which are particularly preferably used are those of the general formula IVb):

$$Si[(CH_2)_nY]_4 \qquad (IVb)$$

in which
Y represents —CH=$CH_2$ and
n represents 1, 2, 3 or 4,
or in which
Y represents $Si[(CH_2)_mCH=CH_2]_3$ and
m represents 1, 2, 3 or 4,
or in which
Y $Si[(CH_2)_mSi[(CH_2)_pCH=CH_2]_3]_3$,
p represents 1, 2, 3 or 4 and
m has the above meaning.

As mentioned above, in the method according to the invention, compounds of the general formula (IV) are reacted with compounds of the general formula (V) and in this manner nonionic dendrimeric compounds of the general formula (I) where r=0 are obtained.

According to the invention, the compounds of the general formula (IV) are reacted with compounds of the general formula (V) at temperatures of −100 to 150° C., preferably of −80 to 100° C., and at pressures from standard pressure to 10 bar, preferably at standard pressure. The molar ratio of compounds of the general formula (IV) to compounds of the general formula (V) during the reaction is generally such that at least one equivalent of the compound of the formula (V) is available for each residue $CR^8$=$CR^9R^{10}$ of the formula (IV).

The reaction is optionally performed in the presence of solvents and/or diluents, such as for example alkanes. In many cases, however, it is also possible to dispense with the use of solvents and/or diluents. This is the case, for example, if an unsaturated compound of the formula (IV) is reacted with $HBCl_2$. The necessary $HBCl_2$ may, for example, be produced during the reaction as an intermediate from trialkylsilanes, $R_3Si$—H and $BCl_3$. This method of preparation is described, for example, in *J. Org. Chem.* 1990, 55, 2274.

In order to produce dendrimeric compounds of an ionic structure of the general formula (I) (in the event that r=1), the reaction product obtained from compounds of the general formula (IV) and compounds of the general formula (V) is further reacted with organic alkali metal, alkaline earth metal or transition metal compounds of the formula (VI) or (VII).

The reaction proceeds in this case at temperatures of −100 to +200° C. and standard pressure, preferably at −100 to 150° C. Solvents and/or diluents which may be considered are those stated above in the quantities which have likewise been stated above.

The compounds of the formulae (VI) or (VII) are preferably used in an equimolar ratio or an excess relative to the residue $Me^2R^2R^3$ of the dendrimeric compounds of the formula (I) where r=0 obtained from the reaction of compounds of the formula (IV) with compounds of the formula (V).

Production of the starting compounds of the formula (IV) is known and may proceed in a similar manner to the production of carbosilane dendrimers. Instructions for the production of carbosilane dendrimers may be found, for example, in *Rubber Chem. Technol.* 1992, 65, 303–314, *Adv. Mater.* 1993, 5, 466–468, *Macromolecules* 1993, 26, 963–968, *J. Chem. Soc., Chem. Commun.* 1994, 2575–2576, *Organometallics* 1994, 13, 2682–2690, *Macromolecules* 1995, 28, 6657–6661 and *Organometallics* 1995, 14, 5362–5366.

During such production, an alkenylsilane, such as for example tetravinyl- or tetrallylsilane, is reacted with a hydrochlorosilane, such as $HSiCl_3$, $MSiMeCl_2$ or $MSiMe_2Cl$, and the resultant product is further reacted with an alkenylmagnesium compound (Grignard reaction). This reaction sequence (hydrosilylation with a Grignard reaction) may be repeated twice or more.

Preferred starting compounds of the formula (IV) which may be considered are:
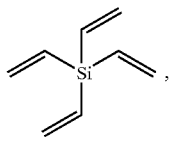 (A)
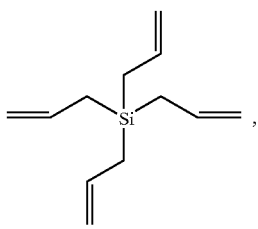 (B)
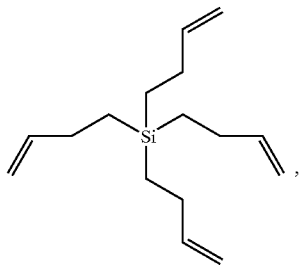 (C)
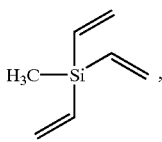 (D)
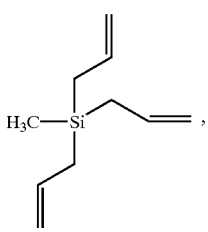 (E)
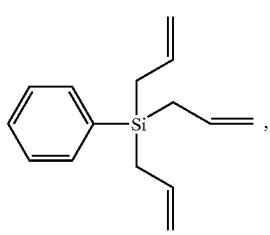 (F)
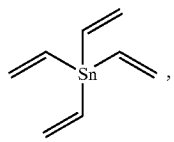 (G)
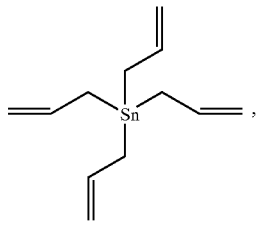 (H)
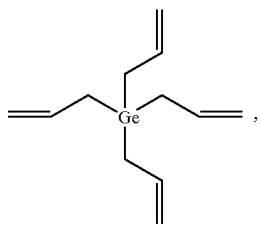 (I)
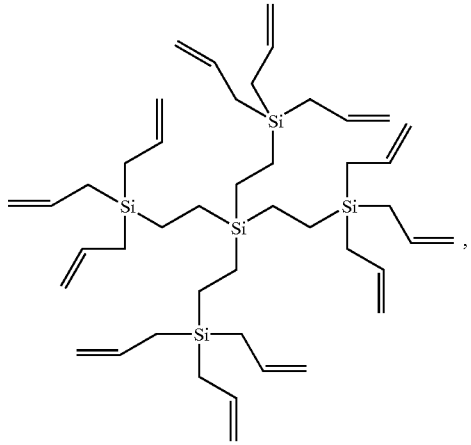 (J)
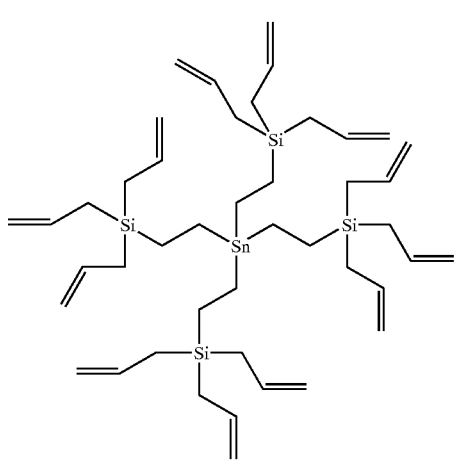 (K)

(L)
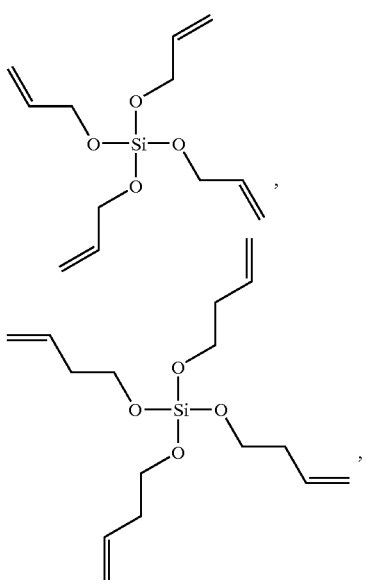
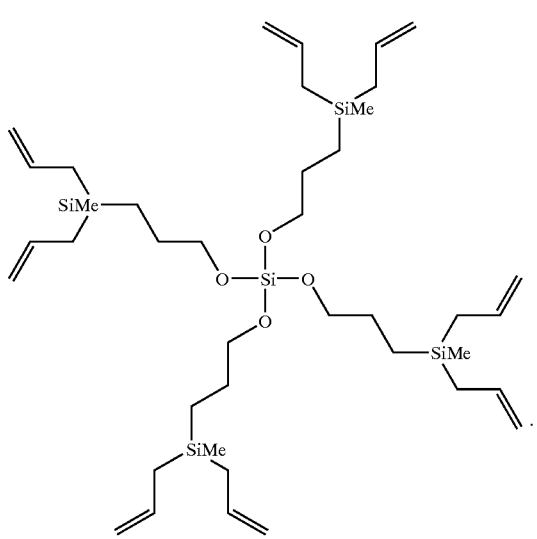
(M)
(N)
Production of the compounds of the formula (I) according to the invention may be illustrated by the following reaction scheme:
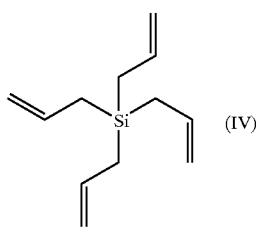
(IV)
Generation zero
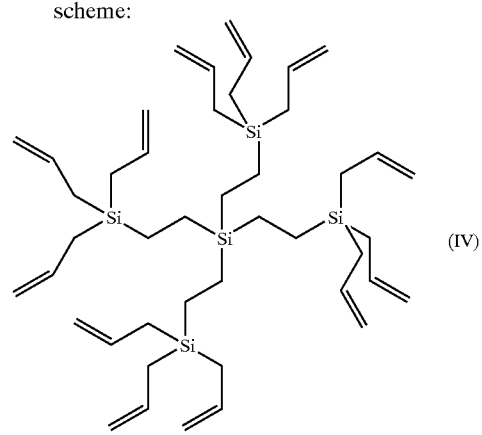
(IV)
Generation 1
↓ boron trichloride/triethylsilane
↓ boron trichloride/triethylsilane
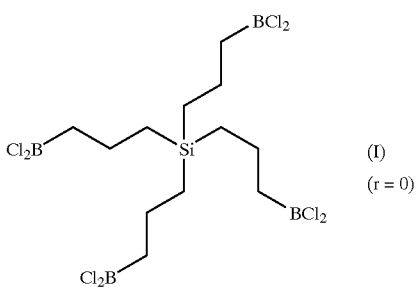
(I) (r = 0)
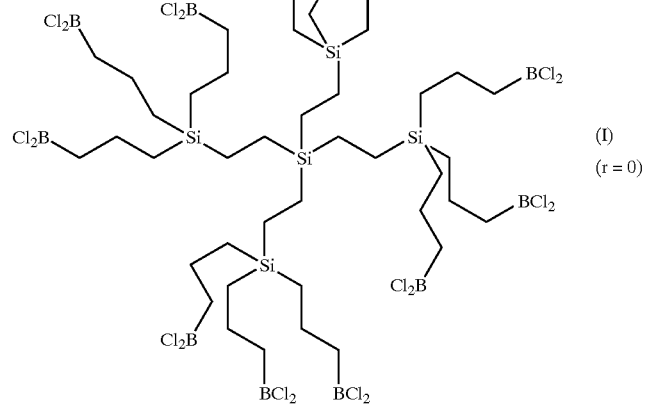
(I) (r = 0)
↓ 1. Li pentafluorophenyl
2. dimethylanilimium chloride
↓ butyllithium

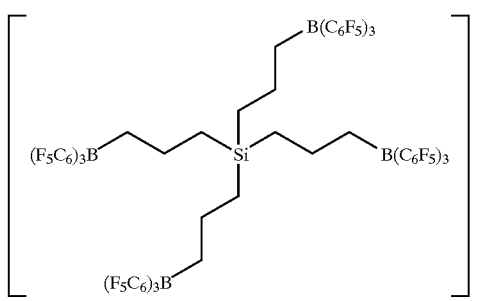

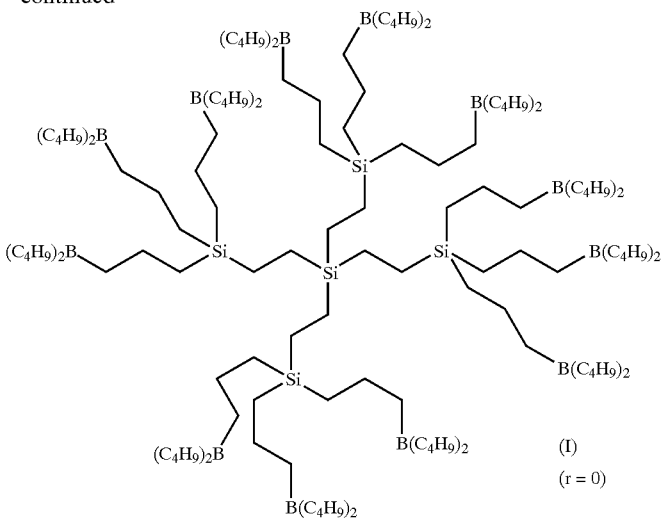

Figure

The novel dendrimeric compounds of the formula (I) may be used as catalysts or for the production of catalyst systems based on transition metal complexes. The stated use of the compounds of the formula (I) according to the invention is not restricted by the appended condition included in the formula (I).

Catalyst systems based on transition metal complexes and the stated dendrimeric compounds of the unrestricted formula (I) consist, for example, of a) a transition metal complex of the formula (VIII)

$$A_c Me^5 R^{12}{}_d \quad (VIII),$$

in which
$Me^5$ represents a transtion metal of groups IIIb to VIIb or of group VIII of the periodic system of elements according to IUPAC nomenclature,
A represents an optionally singly- or multiply bridged anionic ligand
$R^{12}$ has the same meaning as $R^1$, and
c, d represent an integer from 0 to 6 and b) a dendrimeric compound of the formula (I),
wherein the molar ratio of component a) to component b) is conventionally in the range from 1:0.01–1:100, preferably from 1:0.1–1:1.

Transition metal complexes of the formula (VIII) which may in particular be considered are those in which
$Me^5$ is an metal from the group titanium, zirconium, hafnium, vanadium, niobium and tantalum,
A is a pyrazolate of the formula $N_2C_3R^{13}{}_3$
a pyrazolylborate of the formula $R^{14}B(N_2C_3R^{13}{}_3)_3$,
an alkoxide or phenolate of the formula $OR^{14}$,
a siloxane of the formula $OSiR^{14}{}_3$,
a thiolate of the formula $SR^{14}$,
an acetylacetonate of the formula $(R^{14}CO)_2CR^{14}$,
a diimine of the formula $(R^{15}N=CR^{14})_2$,
an amidinate of the formula $R^{14}C(NR^{15}{}_2)_2$,
a cyclooctatetraenyl, an optionally mono- or polysubstitulted cyclopetitadienyl, an optionally mono- or polysubstituted indenyl and an optionally mono- or polysubstituted fluorenyl, wherein substituents which may be considered are a $C_1$ to $C_{20}$ alkyl group, a $C_1$–$C_{10}$ alkoxy group, a $C_6$ to $C_{20}$ aryl group, a $C_6$ to $C_{10}$ aryloxy group, a $C_7$ to $C_{40}$ arylalkyl group, a $C_7$–$C_{40}$ alkylaryl group, a boranyl, silyl, amino or phosphinyl group optionally substituted by $C_1$ to $C_{10}$ hydrocarbon residues, $R^{12}$ represents hydrogen, fluorine, chlorine, bromine, methyl, benzyl, neopentyl and phenyl,
$R^{13}$ in the formulae for A represents hydrogen or a $C_1$–$C_{10}$ alkyl group,
$R^{14}$, $R^{15}$ in the formulae for A have the same meaning as $R^1$,
c represents 1 or 2 and
d represents 2 or 3.

Preferred transition metal complexes of the formula (VIII) are those in which
$Me^5$ represents titanium, zirconium and hafnium,
A represents bis(trimethylsilyl)amide, dimethylamide, diethylamide, diisopropylamide, 2,6-di-tert.-butyl-4-methylphenolate, cyclooctatetraenyl, cyclopentadienyl, methylcyclopentadienyl, benzylcyclopentadienyl, n-propylcyclopentadienyl, n-butylcyclopentadienyl, isobutylcyclopentadienyl, t-butylcyclopentadienyl, cyclopentylcyclopentadienyl, octadecylcyclopentadienyl, 1,2-dimethylcyclopentadienyl, 1,3-dimethylcyclopentadienyl, 1,3-diisopropylcyclopentadienyl, 1,3-di-t-butylcyclopentadienyl, 1-ethyl-2-methylcyclopentadienyl, 1-isopropyl-3-methylcyclopentadienyl, 1-(n-butyl)-3-methylcyclopentadienyl, 1-(t-butyl)-3-methylcyclopentadienyl, pentamethylcyclopentadienyl, 1,2,3,4-tetramethylcyclopentadienyl, 1,2,4-trimethylcyclopentadienyl, 1,2,4-triisopropylcyclopentadienyl, 1,2,4-tri-(t-butyl) cyclopentadienyl, indenyl, tetra-hydroindenyl, 2-methyl indenyl, 4,7-dimethylindenyl, 2-methyl-4,5-benzoindenyl, 2-methyl-4-phenylindenyl, fluorenyl or 9-methylfluorenyl,
$R^{12}$ represents chlorine, methyl or benzyl,
c represents 1 or 2 and
d represents 2 or 3, and the anionic ligands A may be bridged by divalent groups such as $Me_2Si$, $Ph_2Si$, $Ph(Me)Si$, $Me_2C$, $Ph_2C$, $Ph(Me)C$ or $CH_2CH_2$. Examples of the stated transition metal compounds in which c=2 are described, inter alia, in EP 129 368, EP 351 392, EP 485 821, EP 485 823, EP 549 990, EP 659 758. Examples of the stated transition metal compounds in which c=1 are described, inter alia, in *Macrormol. Chem. Rapid Conimun.* (13) 1992, 265 and, in the case of bridged monocyclopentadienyl complexes, in EP 416 815, WO 91/04257 or WO 96/13529.

Further transition metal complexes of the formula (VIII) which may be considered are those in which $Me^5$ represents nickel and palladium, A represents a diimine of the formula $(R^{15}N=CN^{14})_2$, c represents 1 and d represents 2, and $R^{12}$, $R^{14}$, $R^{15}$ have the above-stated meaning.

Examples of the stated diimine complexes are described, inter alia, in WO 96/23010.

Organoaluminum compounds may optionally additionally be added to the catalyst system comprising transition metal complexes and the dendrimers according to the invention. Examples of organoaluminium compounds are trialkylaluminum compounds, such as trimethylaluminium, triethylaluminum, triisobutlaluminum, triisooctylaluminum as well as dialkylaluminum compounds, such as diisobutyl-laluminum hydride, or aluminoxanes, such as trimethylaluminoxane or triisobutylaluminoxane. The molar ratio of the organoaluminum compounds to transition metal complexes of the formula (VIII) is in the range from 10000:1–0.1:1, preferably from 1000:1–1:1, particularly preferably from 100:1–10:1.

The present invention also provides the use of the novel catalysts or catalyst systems for the polymerization of unsaturated organic compounds, in particular of olefins and dienes. Polymerization is here taken to mean both homo- and copolymerization of the stated unsaturated compounds. $C_2$–$C_{10}$ alkenes, such as ethylene, propylene, 1-butene, 1-pentene and 1-hexene, 1-octene, isobutylene and arylalkenes, such as styrene, are in particular used in said polymerization. Dienes which are in particular used are: conjugated dienes, such as 1,3-butadiene, isoprene, 1,3-pentadiene, and unconjugated dienes, such as 1,4-hexadiene, 1,5-heptadiene, 5,7-dimethyl-1,6-octadiene, 4-vinyl-1-cylohexene, 5-ethylidene-2-norbornene, 5-vinyl-2-norbornene and dicyclopentadiene.

As mentioned above, however, the novel dendrimeric compounds of the formula (I) may also be used on their own as catalysts, for example for polymerization reactions. The dendrimeric compounds of the formula (I) are suitable not only for polymerizing unsaturated compounds, but also for polymerizing cyclic ethers, such as ethylene oxide, propylene oxide and tetrahydrofuran.

The catalysts according to the invention are in particular suitable for the production of rubbers based on copolymers of ethylene with one or more of the stated α-olefins and the stated dienes. The catalyst system according to the invention is furthermore suitable for polymerizing cycloolefins, such as norbornene, cyclopentene, cyclohexene or cyclooctane and for copolymerizing cycloolefins with ethylene or α-olefins.

Polymerization may be performed in the liquid phase, in the presence or absence of an inert solvent, or in the gas phase. Suitable solvents are aromatic hydrocarbons, such as benzene and/or toluene, or aliphatic hydrocarbons, such as propane, hexane, heptane, octane, isobutane, cyclohexane, or mixtures of the various hydrocarbons.

It is possible to use the catalyst system according to the invention applied onto a support. Suitable support materials which may be mentioned are, for example, inorganic or organic polymeric supports, such as silica gel, magnesium chloride, zeolites, carbon black, activated carbon, aluminum oxide, polystyrene and polypropylene.

Polymerization is generally performed at pressures of 1 to 1000, preferably of 1 to 100 bar, and temperatures of −100° C. to +250° C., preferably of 0° C. to +150° C. Polymerization may be performed continuously or discontinuously in conventional reactors.

The novel dendrimeric compounds of the formula (I) are distinguished by elevated thermal stability and storage stability. They are produced from inexpensive educts which are industrially available in large quantities. The production method described above provides wide scope for various structural variants of the dendrimeric compound of the formula (I), which have a defined molecular structure. The optimum structure may accordingly be tailored to the intended application.

In combination with transition metal complexes of the formula (VIII), the novel dendrimeric compounds have elevated catalytic activity for the polymerization of unsaturated compounds. They moreover have improved catalyst service lives, i.e. consistently high catalytic activity over extended periods of polpymerization. Due to their elevated catalytic activity, only small quantities of the dendrimeric compounds are required. The residual catalyst content in the polymer is so low that no work-up is required to remove the catalyst. This gives rise to a processing advantage as a costly washing step to remove the catalyst is omitted.

Another advantage is the favourable molar ratio of transition metal complexes of the formula (VIII) to dendrimeric compounds of the formula (I) in the production of catalyst system. Highly reproducible catalytic activities are obtained if the dendrimeric compounds are used in a molar deficit relative to the transition metal complex.

No preactivation is required when the dendrimeric compounds of the formula (I) are used to produce catalyst systems. For example, olefins may be polymerized as follows: after the conventional cleaning operations, a steel autoclave is filled with a solvent and a scavenger, for example triisobutyaluminum. The scavenger renders harmless any possible contaminants and catalyst poisons, for example water or other compounds containing oxygen. A compound of the formula (VIII) is then added as a catalyst precursor. The reactor is then filled with monomers and polymerization is started by adding a solution of the dendrimeric compounds described above. Separate feeding of the dendrimeric compound without preactivation is of particular advantage in a continuous polymerization process.

The invention is illustrated in greater detail by the following Examples.

General Information

The organometallic compounds were produced and handled under a protective argon atmosphere and with the exclusion of air and moisture (Schlenk technique). All the necessary solvents were obtained in absolute form before use by boiling for several hours over a suitable desiccant and subsequent distillation under argon. The compounds were preferably characterized by $^{11}B$ NMR, optionally also by $^1H$ NMR and $^{13}C$ NMR. Other commercial educts were used without further purification. Tetraallylsilane was produced from silicon tetrachloride and allylmagnesium chloride.

EXAMPLE 1

Production of $Si[(CH_2)_3BCl_2]_4$ 23.5 g (0.2 mol) of boron trichloride were condensed at −65° C. into a flask equipped with a gas inlet, reflux condenser and internal thermometer. A mixture of 23.3 g (0.2 mol) of triethylsilane and 9.6 g (0.05 mol) of tetraallylsilane were then slowly added dropwise at this temperature. On completion of addition, the mixture was heated to room temperature. Volatile constituents (substantially triethylchlorosilane) were then removed under a 0.2 mbar vacuum, initially at room temperature, then at a bath temperature of 40° C. The product was obtained as a colourless, highly mobile oil.

$C_{12}H_{24}B_4Cl_8Si$, M=523.271 g/mol; $^1H$ NMR (CDCl$_3$): δ=0.52 ppm (m, 2H, Si—CH$_2$), 1.55 ppm (m, 4H, Cl$_2$B—CH$_2$—CH$_2$); $^{13}C\{^1H\}$ NMR: δ=15.4 ppm (Si—CH$_2$), 20.0 ppm (Si—CH$_2$—$\underline{C}$H$_2$), 34.2 ppm (B—CH$_2$); $^{11}B\{^1H\}$ NMR: δ =63.1 ppm.

EXAMPLE 2

Production of a Solution of $Si[(CH_2)_3B(C_6F_5)_3]_4^{4-}4Li^+$ 6.35 ml of n-butyllithium (1.6 M in hexane; 10.1 mmol) were added dropwise within 20 minutes at −70° C. to a solution of 2.5 g (10.1 mmol) of bromopentafluorobenzene in 60 ml of hexane. The resultant suspension was stirred for 2 hours at −70° C. A solution of 445 mg (0.85 mmol) of $Si[(CH_2)_3BCl_2]_4$ from Example 1 in 5 ml of hexane was then added dropwise within 5 minutes and the reaction solution was then slowly raised to room temperature within 3 hours and stirred overnight.

EXAMPLE 3

Production of $Si[(CH_2)_3B(C_6F_5)_3]_4^{4-}4C_6H_5—NH(CH_3)_2^+$ 536 mg (3.4 mmol) of dimethylanilinium hydrochloride in 20 ml of methylene chloride were added to a solution of $Si[(CH_2)_3B(C_6F_5)_3]_4^{4-}4Li^+$, produced as in Example 2. The mixture was again stirred overnight and the volatile constituents removed under a vacuum. After addition of 40 ml of methylene chloride, the mixture was filtered through diatomaceous earth and volatile constituents were removed from the colourless filtrate under a vacuum. After washing twice with 20 ml portions of hexane, the product was obtained as a colourless wax. $C_{116}H_{72}B_4F_{60}N_4Si$, M=2733.170 g/mol $^{11}B\{^1H\}$ NMR (CD$_2$Cl$_2$): δ=−13.4 ppm.

EXAMPLE 4

Polymerization of Ethylene 500 ml of toluene, 0.1 ml of TIBA and 1 ml of a solution of 12.4 mg of bis(cyclopentadienyl)zirconiumdimethyl in 24.7 ml of toluene (=1 μmol of bis(cyclopentadienyl) zirconiumdimethyl) were initially introduced into a 1.4 L steel autoclave. This solution was adjusted to a temperature of 60° C. Ethylene was then apportioned until the internal pressure in the reactor rose to 6 bar. Polymerization was started by adding 1 ml of a solution of 57.4 mg of the compound from Example 3 in 42 ml of toluene (=0.5 μmol of $Si[(CH_2)_3B(C_6F_5)_3]_4^{4-}4C_6H_5—NH(CH_3)_2^+$. After 20 minutes' polymerization at 60° C. and 6 bar, the autoclave was depressurised, the polymer filtered off, washed with methanol and dried for 20 h under a vacuum at 60° C. 36.6 g of polyethylene were obtained.

EXAMPLE 5

Copolymerization of Ethylene and 1-Hexene 100 ml of toluene, 0.1 ml of TIBA and 5 ml of 1-hexene were initially introduced into a 250 ml glass reactor. 1 ml of a solution of 12.7 mg of ethylenebis(indenyl)-zirconiumdimethyl in 16.8 ml of toluene (=1 μmol of ethylenebis(indenyl)-zirconiumdimethyl) was then added. Ethylene was then continually introduced into the solution at 20° C. via a gas inlet tube at a pressure of 1.1 bar. Polymerization was started by adding 1 ml of solution of 57.4 mg of the compound from Example 3 in 42 ml of toluene (=0.5 μmol of $Si[(CH_2)_3B(C_6F_5)_3]_4^{4-}4C_6H_5—NH(CH_3)_2^+$). At a temperature of 20° C. and a pressure of 1.1 bar, a highly viscous clear reaction solution was obtained after 30 minutes' polymerization. Polymerization was terminated by adding 100 ml of methanol. The precipitated polymer was filtered off, washed with methanol and dried in a vacuum drying cabinet. 5.44 g of ethylene/1-hexene copolymer were obtained which contained 14.4 mol % of 1-hexene (according to the $^{13}C$ NMR spectrum).

EXAMPLE 6

Polymerization of Propylene

Production of the catalyst solution: a solution of 5 μmol of dimethylsilylbis(indenyl)zirconium dichloride in 5 ml of toluene was combined with 10 μmol of triethylaluminum and stirred for 20 minutes at 20° C. 5 ml of a solution of 57.4 mg of the compound from Example 3 in 42 ml of toluene were then added (=2.5 μmol of $Si[(CH_2)_3B(C_6F_5)_3]_4^{4-}4C_6H_5—NH(CH_3)_2^+$) and the mixture stirred for 5 minutes.

Polymerization: 100 ml of hexane, 0.1 ml of TIBA and the catalyst solution were initially introduced into a 250 ml glass reactor. Propylene was then continuously introduced into the solution at 40° C. via a gas inlet tube at a pressure of 1.1 bar. After 30 minutes' polymerization, the reaction was terminated by adding 100 ml of methanol. The precipitated polymer was filtered off, washed with methanol and dried in a vacuum drying cabinet. 4.4 g of polypropylene powder were obtained.

EXAMPLE 7

Terpolymerisation of Ethylene, Propylene and 5-Ethylidene-2-norbornene 500 ml of hexane, 1 ml of triisobutylaluminum and 0.5 ml of a solution of 41.8 mg of a ethylenebis(tetrahydroindenyl) zirconium dichloride in 9 ml of triisobutylaluminum and 40 ml of hexane (=1 μmol of ethylenebis(tetrahydroindenyl) zirconium dichloride) were initially introduced into a 1.4 L steel autoclave equipped with a mechanical stirrer, manometer, temperature sensor, temperature controller, catalyst lock and monomer feed devices for ethylene and propylene. 51 g of propylene and 5 ml of 5-ethylidene-2-norbornene were then apportioned. The internal temperature was adjusted to 40° C. with a thermostat. Ethylene was then apportioned until the internal pressure in the reactor rose to 4 bar. Polymerization was started by adding 2 ml of a solution of 57.4 mg of the compound from Example 3 in 42 ml of toluene (=1 μmol of $Si[(CH_2)_3B(C_6F_5)_3]_4^{4-}4C_6H_5—NH(CH_3)_2^+$) and ethylene was continuously apportioned such that the internal pressure at 40° C. remained constant at 4 bar. After 50 minutes' polymerization, the autoclave was depressurised and the polymer solution combined with a 0.1 wt. % solution of Vulkanox BKF in hexane, the mixture stirred for 10 min and the polymer then precipitated with methanol. The resultant polymer was isolated and dried for 20 h under a vacuum at 60° C. 80.1 g of terpolymer were obtained having the following composition according to IR spectroscopy: 58.9% ethylene, 35.5% propylene and 5.6% ENB. A Tg of −49° C. was determined by the DSC method.

EXAMPLE 8

Reaction of $Si[(CH_2)_3B(C_6F_5)_3]_4{}^{4-}4Li^+$ with Trityl Chloride

A solution of 948 mg (3.4 mmol) of trityl chloride in 20 ml of methylene chloride were added dropwise within 15 min to a solution of $Si[(CH_2)_3B(C_6F_5)_3]_4{}^{4-}4Li^+$, produced according to Example 2, and.the reaction batch stirred for 14 h at 25° C. The solvent was then removed to dryness by distillation under a vacuum and the residue combined with 40 ml of methylene chloride. A dark red coloured solution containing finely divided solid was obtained, said solid being separated by decanting and subsequent filtration. The clear solution was again evaporated to dryness under a vacuum, the red oily residue was washed twice with 40 ml portions of n-hexane, the hexane decanted and the solid again dried under at vacuum at 25° C. A reddish coloured, slightly tacky product was obtained.

$^{11}B$ $\{^1H\}$ NMR $(CD_2Cl_2)$: δ=1.4 ppm.

EXAMPLE 9

Polymerization of Ethylene 100 ml of toluene, 0.1 ml of triisobutylaluminum and 1 ml of solution of 27.2 mg of bis(indenyl)zirconium dimethyl in 15.5 ml of toluene (=5 μmol of bisindenylzirconiumdimethyl) were initially introduced into a 250 ml glass reactor. Ethylene was then continually introduced into the solution at via a gas inlet tube at a pressure of 1.1 bar. Polymerization was started by adding a solution of 15.9 mg of the product from Example 8 in 1 ml of toluene. At a temperature of 40° C. and an ethylene pressure of 1.1 bar, the reaction was terminated after 15 minutes' polymerization by adding 10 ml of methanol, the polymer was filtered off, washed with methanol and dried in a vacuum drying cabinet. 1.72 g of highly crystalline polyethylene were obtained having a melting point of +136.5° C. and a heat of fusion of 306 J/g (on first heating) as measured by DSC.

EXAMPLE 10

Copolymerization of Ethylene and Propylene 100 ml of toluene, 0.1 ml of TIBA and 1 ml of a solution of 20.1 mg of ethylene-bis(indenyl)zirconiumdimethyl in 10.6 ml of toluene (=5 μmol of ethylenebis-(indenyl) zirconiumdimethyl) were initially introduced into a 250 ml glass reactor. An ethylene/propylene mixture (1:1 molar ratio) was then continually introduced at 20° C. into the solution via a gas inlet tube at a pressure of 1.1 bar. Polymerization was started by adding a solution of 16.9 mg of the product from Example 8 in 1 ml of toluene. At a temperature of 20° C. and a pressure of 1.1 bar, a highly viscous clear reaction solution was obtained after 1 hour's polymerization. Polymerization was terminated by adding 100 ml of methanol. The precipitated, elastic polymer was filtered off, washed with methanol and dried in a vacuum drying cabinet. 22.5 g of amorphous ethylene/propylene copolymer were obtained.

EXAMPLE 11

Production of $Si[(CH_2)_3B(3,5-(CF_3)_2C_6H_3)_3]_4{}^{4-}4Li^+$

The solvent was removed from 15.6 ml of n-butyllithium (1.6 M in hexane, 25 mmol) under a vacuum at 0° C. After cooling to −75° C., 50 ml of diethyl ether, which had been precooled to −50° C., were added and stirred until the n-butyllithium had completely redissolved. After addition of 4.3 ml (7.3 g; 25 mmol) of bromo-3,5-bis(trifluoromethyl) benzene, the reaction mixture was stirred for a further 15 minutes at −75° C. and then 1.1 g (2.1 mmol) of $Si[(CH_2)_3BCl_2]_4$ from Example 1 were added. After 1hour's stirring, the mixture was heated to room temperature and stirred overnight. The reaction mixture was then poured into approx. 100 ml of iced water, the aqueous phase was extracted twice with 50 ml portions of ether and the extract washed once with saturated NaCl solution and once with water. After drying over sodium sulfate and removal of the solvent under a vacuum, the product was obtained as a colourless oil.

$C_{108}H_{60}B_4F_{72}Si$, M=2824.751 g/mol; $^{11}B\{^1H\}$ NMR $(CD_2Cl_2)$: δ=−9.9 ppm.

EXAMPLE 12

Production of $Si[(CH_2)_3B(3,5-(CF_3)_2C_6H_3)_3]_4{}^{4-}4C_6H_5—NH(CH_3)_2{}^+$ The solvent was removed from 15.6 ml of n-butyllithium (1.6 M in hexane, 25 mmol) under a vacuum at 0° C. After cooling to −75° C., 50 ml of diethyl ether, which had been precooled to −50° C., were added and stirred until the n-butyllithium had completely redissolved. After addition of 4.3 ml (7.3 g; 25 mmol) of bromo-3,5-bis(trifluoromethyl) benzene, the reaction mixture was stirred for a further 15 minutes at −75° C. and then 1.1 g (2.1 mmol) of $Si[(CH_2)_3BCl_2]_4$ from Example 1 were added. After 1 hour's stirring, the reaction mixture was heated to room temperature and, after addition of 1.3 g (8.33 mmol) of dimethylanilinium hydrochloride, stirred overnight. The volatile constituents were then removed under a vacuum and the residue extracted with 40 ml of methylene chloride. After filtration and removal of the solvent by distillation, the product was obtained as a colourless oil.

$^{11}B$ $\{^1H\}$ NMR $(CD_2Cl_2)$: δ=−9.9 ppm.

EXAMPLE 13

Production of $Si[(CH_2)_3B(3,5-(CF_3)_2C_6H_3)_3]_4{}^{4-}4(C_6H_5)_3C^+$

The solvent was removed from 15.6 ml of n-butyllithium (1.6 M in hexane, 25 mmol) under a vacuum at 0° C. After cooling to −75° C., 50 ml of diethyl ether, which had been precooled to −50° C., were added and stirred until the n-butyllithium had completely redissolved. After addition of 4.3 ml (7.3 g; 25 mmol) of bromo-3,5-bis(trifluoromethyl) benzene, the reaction mixture was stirred for a further 15 minutes at −75° C. and then 1.1 g (2.1 mmol) of $Si[(CH_2)_3BCl_2]_4$ from Example 1 were added. After 1 hour's stirring, the reaction mixture was heated to room temperature and stirred for a further 60 hours. After removal of the volatile constituents by distillation under a vacuum, 40 ml of hexane and 2.3 g (8.3 mmol) of trityl chloride were added and the reaction mixture refluxed overnight. After cooling to room temperature, the volatile constituents were removed under a vacuum and the residue extracted with 40 ml of methylene chloride. After filtration and removal of the solvent by distillation, the product was obtained as a yellow oil.

$^{11}B\{^1H\}$ NMR $(CD_2Cl_2)$: δ=−10.0 ppm.

EXAMPLE 14

Production of $Si[(CH_2)_2Si(C_3H_5)_3]_4$ $(Si[(CH_2)_2SiCl_3]_4$ was produced as described in *Organometallics* 1994, 13, 2682–2690.)

77.2 g (3.2 mol) of magnesium chips were suspended in 1900 ml of absolute THF and cooled to 0° C. At 0 to 5° C., 131.4 g (1.7 mol) of freshly distilled allyl chloride were added dropwise (the reaction began as soon as a few ml of allyl chloride had been added). Once addition was complete, the reaction mixture was heated to room temperature and then refluxed for 2 hours. After cooling, 143.6 g (0.21 mol) of Si[(CH$_2$)$_2$SiCl$_3$]$_4$ in 100 ml of THF were added dropwise, wherein the temperature rose to 35° C. After addition, the reaction mixture was stirred overnight and then diluted with 1200 ml of hexane. After hydrolysis with 1200 ml of water, the separated organic phase was washed three times with 1000 ml portions of water and once with a saturated sodium chloride solution. After drying over MgSO$_4$ and removal of the volatile constituents by distillation under a vacuum, the product was obtained as a pale yellow oil.

EXAMPLE 15

Production of Si[(CH$_2$)$_2$Si[(CH$_2$)$_3$BCl$_2$]$_3$]$_4$ 23.5 g (0.2 mol) of boron trichloride were condensed at −65° C. into a flask equipped with a gas inlet, reflux condenser and internal thermometer. At this temperature, a mixture of 23.3 g (0.2 mol) of triethylsilane and 12.4 g (166 mmol) of Si[(CH$_2$)$_2$Si(C$_2$H$_5$)$_3$]$_4$ from Example 14, was then slowly added drop wise. Once addition was complete, the mixture was heated to room temperature and stirred overnight. Volatile constituents (substantially triethylchlorosilane) were then removed under a 0.2 mbar vacuum, initially at room temperature, then at a bath temperature of 40° C. The product was obtained as a colourless oil, some of which crystallised on the flask wall.

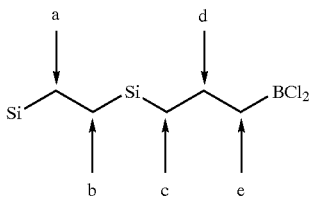

C$_{44}$H$_{88}$B$_{12}$Cl$_{24}$Si$_5$, M=1738.199 g/mol; $^1$H NMR (CD$_2$Cl$_2$): δ=0.4 ppm (m, 4H, Si—C$^a$H$_2$—C$^b$H$_2$—Si), 0.5 ppm (m, 6H, Si—C$^c$H$_2$), 1.6 ppm (m, 12H, C$^d$H$_2$—C$^e$H$_2$—BCl$_2$); $^{13}$C{$^1$H} NMR: δ=3.3 ppm (Si—C$^a$H$_2$), 4.77 ppm (Si—C$^b$H$_2$), 15.1 ppm (Si—C$^c$H$_2$), 20.1 ppm (C$^d$H$_2$), 34.4 ppm (wide signal, B—C$^e$H$_2$); $^{11}$B{$^1$H} NMR: δ=63.1 ppm.

EXAMPLE 16

Production of Si[(CH$_2$)$_2$Si[(CH$_2$)$_3$B(C$_4$H$_9$)$_2$]$_3$]$_4$

A solution of 487 mg (0.28 mmol) of Si[(CH$_2$)$_2$Si[(CH$_2$)$_3$BCl$_2$]$_3$]$_4$ in 5 ml of hexane was rapidly added at −70° C. to a mixture of 4.2 ml of n-butyllithium (1.6 M in hexane, 6.7 mmol) in 60 ml of hexane. After 30 minutes' stirring, the mixture was first heated to room temperature and finally refluxed for a further 2 hours. Once the volatile constituents had been removed by distillation under a vacuum, 40 ml of methylene chloride were added and the mixture filtered through diatomaceous earth. After removal of the volatile constituents by distillation, the product was obtained as a light yellow oil.

$^{11}$B{$^1$H} NMR (CD$_2$Cl$_2$): δ=+86.8 ppm.

EXAMPLE 17

Production of Si[(CH$_2$)$_2$Si[(CH$_2$)$_3$B(C$_6$F$_5$)$_3$]$_3$]$_4$$^{12-}$ 12C$_6$H$_5$—NH(CH$_3$)$_2$$^+$ 6.35 ml of n-butyllithium (1.6 M in hexane; 10.1 mmol) were added dropwise within 20 minutes at −70° C. to a solution of 2.5 g (10.1 mmol) of bromopentafluorobenzene in 60 ml of hexane. The resultant suspension was stirred for 2 hours at −70° C. A solution of 487 mg (0.28 mmol) of Si[(CH$_2$)$_2$Si[(CH$_2$)$_3$BCl$_2$]$_3$]$_4$ from Example 15 in 5 ml of hexane was then added dropwise within 5 minutes and the reaction solution then slowly heated to room temperature within 3 hours and stirred overnight. After addition of 536 mg (3.4 mmol) of dimethylanilinium hydrochloride in 20 ml of methylene chloride, the mixture was again stirred overnight and finally the volatile constituents removed by distillation under a vacuum. After addition of 40 ml of methylene chloride, the mixture was filtered through diatomaceous earth and the volatile constituents removed from the colourless filtrate under a vacuum. After washing twice with 20 ml portions of hexane, the product was obtained as a colourless wax.

C$_{356}$H$_{232}$B$_{12}$F$_{180}$N$_{12}$Si$_5$, M=8367.896 g/mol $^{11}$B{$^1$H} NMR (CD$_2$Cl$_2$): δ=−13.2 ppm.

EXAMPLE 18

Polymerization of Ethylene

The polymerization from Example 9 was repeated, with the difference that 1 ml of a solution of 132 mg of the compound from Example 17 in 31.6 ml of methylene chloride (=0.5 μmol of Si[(CH$_2$)$_2$Si[(CH$_2$)$_3$B(C$_6$F$_5$)$_3$]$_3$]$_4$$^{12-}$ 12C$_6$H$_5$—NH(CH$_3$)$_2$$^+$) was used instead of the solution of the compound from Example 8. 2.1 g of polyethylene were obtained.

EXAMPLE 19

Copolymerization of Ethylene and Propylene 500 ml of hexane and 0.1 ml of triisobutylaluminum were initially introduced into a 1.4 L steel autoclave equipped with a mechanical stirrer, manometer, temperature sensor, temperature controller, catalyst lock and monomer feed devices for ethylene and propylene. 0.5 ml of a solution of 41.8 mg of ethylenebis(tetrahydroindenyl)zirconium dichloride in 9 ml of triisobutylaluminum and 40 ml of hexane (=1 μmol of ethylenebis(tetrahydroindenyl)zirconium dichloride) were added thereto. 51 g of propylene were then apportioned. The internal temperature was adjusted to 40° C. with a thermostat. Ethylene was then apportioned until the internal pressure in the reactor rose to 4 bar. Polymerization was started by adding 0.5 ml of a solution of 132 mg of the compound from Example 17 in 31.6 ml of methylene chloride (=0.25 μmol of Si[(CH$_2$)$_2$Si[(CH$_2$)$_3$B(C$_6$F$_5$)$_3$]$_3$]$_4$$^{12-}$ 12C$_6$H$_5$—NH(CH$_3$)$_2$$^+$) and ethylene was continuously apportioned such that the internal pressure at 40° C. remained constant at 4 bar. After 40 minutes' polymerization, the autoclave was depressurised and the polymer then precipitated with methanol. The resultant polymer was isolated and dried for 20 h under a vacuum at 60° C. 70.1 g of copolymer were obtained having the following composition according to IR spectroscopy: 61.8% ethylene and 38.2% propylene. A Tg of −57° C. was determined by the DSC method.

EXAMPLE 20

Production of Si[(CH$_2$)$_3$B(C$_6$F$_5$)$_3$]$_4$$^{4-}$4H$_3$C—(CH$_2$)$_{10}$—N(CH$_3$)$_2$H$^+$ a) 26.8 ml (42.6 mmol) of a 1.6 molar solution of n-butyllithium in hexane were added dropwise with stirring at −70° C. to 10.5 g (42.6 mmol) of bromopentafluorobenzene in 250 ml of hexane in such a manner that there was no observable rise in temperature. After a further 2 hours' stirring at this temperature, 1.9 g (3.6 mmol) of Si[(CH$_2$)$_3$BCl$_2$]$_4$ in 15 ml of hexane were finally added dropwise, then the reaction mixture was heated to room temperature within 3 hours and stirred for a further 60 hours. A colourless suspension was obtained.

b) 20 g (0.1 mol) of N,N-dimethylundecylamine were added in portions with stirring to 14.8 g (0.15 mol) of concentrated hydrochloric acid (37 wt. %). After the exothermic reaction (up to approx. 35° C.), the highly viscous mixture was diluted with 5 ml of concentrated hydrochloric acid and 5 ml of water, stirred for a further 2 hours and finally left to stand overnight. The aqueous phase was then extracted with 80 ml of methylene chloride, the organic phase dried with sodium sulfate and the solvent removed under a vacuum. In order to remove any traces of water, the residue was resuspended in 80 ml of toluene and concentrated under a vacuum and the operation was then repeated in 100 ml of hexane. Once the solvent had again been removed by distillation under a vacuum, N,N-dimethylundecylammonium hydrochloride was obtained as a colourless solid.

Yield: 17.8 g, corresponding to 75% of theoretical.

c) 3.4 g (14.3 mmol) of N,N-dimethylundecylammonium hydrochloride in 80 ml of methylene chloride were stirred into the solution obtained in a) and stirred for 20 hours at room temperature. The volatile constituents were then removed under a vacuum and the residue extracted with 80 ml of methylene chloride. After filtration and removal of the solvent by distillation under a vacuum, the product was obtained as a light yellow wax.

Yield: 7.0 g, corresponding to 64% of theoretical.

$^{11}$B{$^1$H} NMR (CDCl$_3$): δ=−13.1 ppm.

EXAMPLE 21

Polymerization of Ethylene 100 ml of toluene, 0.1 ml of triisobutylaluminum and 2 ml of a solution of 60.0 mg of bis(indenyl)zirconiumdimethyl in 34.2 ml of toluene (=10 µmol of bisindenylzirconiumdimethyl) were initially introduced into a 250 ml glass reactor. Ethylene was then continually introduced into the solution via a gas inlet tube at a pressure of 1.1 bar. Polymerization was started by adding 0.5 ml of solution of 19.0 mg of the product from Example 20 in 1.25 ml of toluene (=2.5 µmol of Si[(CH$_2$)$_3$B(C$_6$F$_5$)$_3$]$_4$$^{4-}$4CH$_2$(CH$_2$)$_{10}$(CH$_3$)$_2$$^+$). At a temperature of 40° C. and an ethylene pressure of 1.1 bar, the reaction was terminated after 10 minutes' polymerization by adding 10 ml of methanol, the polymer was filtered off, washed with methanol and dried in a vacuum drying cabinet. 1.9 g of polyethylene were obtained.

EXAMPLE 22

Production of Si[(CH$_2$)$_3$B(C$_6$F$_5$)$_3$]$_4$$^{4-}$4H$_3$C—(CH$_2$)$_{11}$—N(CH$_3$)$_2$H$^+$ a) 20.3 ml (32.2 mmol) of a 1.6 molar solution of n-butyllithium in hexane were added dropwise with stirring at −70° C. to 8.0 g (32.2 mmol) of bromopentafluorobenzene in 190 ml of hexane in such a manner that there was no observable rise in temperature. After a further 2 hours' stirring at this temperature, 1.4 g (2.7 mmol) of Si[(CH$_2$)$_3$BCl$_2$]$_4$ in 15 ml of hexane were finally added dropwise, then the reaction mixture was heated to room temperature within 3 hours and stirred for a further 60 hours. A colourless suspension was obtained.

b) 43.3 g (0.2 mol) of N,N-dimethyldodecylamine were added in portions with stirring to 30.0 g (0.3 mol) of concentrated hydrochloric acid (37 wt. %). After the exothermic reaction (up to approx. 35° C.), the highly viscous mixture was diluted with 25 ml of concentrated hydrochloric acid and 25 ml of water and stirred overnight. The aqueous phase was then extracted with 100 ml of methylene chloride, the organic phase was washed once with 50 ml of water, dried with sodium sulfate and the solvent was removed under a vacuum. In order to remove any traces of water, the residue was resuspended in 50 ml of toluene and concentrated under a vacuum and the operation was then repeated in 80 ml of hexane. Once the solvent had again been removed by distillation under a vacuum, N,N-dimethyldodecylammonium hydrochloride was obtained as a colourless solid.

Yield: 27.6 g, corresponding to 55% of theoretical.

c) 2.3 g (10.8 mmol) of N,N-dimethyldodecylammonium hydrochloride in 60 ml of methylene chloride were stirred into the solution obtained in a) and stirred for 20 hours at room temperature. The volatile constituents were then removed under a vacuum and the residue extracted with 80 ml of methylene chloride. After filtration and removal of the solvent by distillation under a vacuum, the product was obtained as a light yellow wax.

Yield: 7.0 g, corresponding to 64% of theoretical.

$^{11}$B{$^1$H} NMR (CDCl$_3$): δ=−13.1 ppm.

EXAMPLE 23

Production of Si{(CH$_2$)$_2$Si[(CH$_2$)$_3$B(C$_6$F$_5$)$_3$]$_3$}$_4$$^{12-}$12H$_3$C—(CH$_2$)$_{10}$—N(CH$_3$)$_2$H$^+$ a) 12.7 ml (20.2 mmol) of a 1.6 molar solution of n-butyllithium in hexane were added dropwise with stirring at −70° C. to 5.0 g (20.2 mmol) of bromopentafluorobenzene in 120 ml of hexane in such a manner that there was no observable rise in temperature. After a further 2 hours' stirring at this temperature, 974 mg (0.6 mmol) of Si{(CH$_2$)$_2$Si[(CH$_2$)$_3$BCl$_2$]$_3$}$_4$ in 10 ml of toluene were finally added dropwise, then the reaction mixture was heated to room temperature within 3 hours and stirred for a further 60 hours. A colourless suspension was obtained.

b) 1.6 g (6.7 mmol) of N,N-dimethylundecylammonium hydrochloride (produced as described in b) in Example 20) in 40 ml of methylene chloride were stirred into the solution obtained in a) and stirred for 20 hours at room temperature. The volatile constituents were then removed under a vacuum and the residue extracted with 60 ml of methylene chloride. After filtration and removal of the solvent by distillation under a vacuum, the product was obtained as a light yellow wax.

Yield: 3.1 g, corresponding to 60% of theoretical.

$^{11}$B{$^1$H} NMR (CDCl$_3$): δ=−13.9 ppm.

EXAMPLE 24

Polymerization of Ethylene

The polymerization from Example 21 was repeated, with the difference that 0.5 ml of a solution of 70 mg of the compound from Example 23 in 2.3 ml of toluene (=1.7 μmol of Si{[(CH$_2$)$_2$Si[(CH$_2$)$_3$B(C$_6$F$_5$)$_3$]$_3$]$_4$$^{12-}$12CH$_3$(CH$_2$)$_{10}$NH (CH$_3$)$_2$$^+$) was used instead of the solution of the compound from Example 21. 1.7 g of polyethylene were obtained.

EXAMPLE 25

Production of Si{(CH$_2$)$_2$Si[(CH$_2$)$_2$Si(C$_3$H$_5$)$_3$]$_3$}$_4$ (Si{(CH$_2$)$_2$Si[(CH$_2$)$_2$SiCl$_3$]$_3$}$_4$ was produced as described in *Organometallics* 1994, 13, 2682–2690).

At an initial temperature of 0° C., 23 ml (21.6 g; 282 mmol) of allyl chloride were added dropwise with vigorous stirring to 22.3 g (919 mmol) of magnesium chips in 400 ml of THF in such a manner that the reaction temperature never exceeded 5° C. (the Grignard reaction was started with a little 1,2-dibromoethane). Once addition was complete, the reaction mixture was heated first to room temperature and was finally refluxed for a further 2 hours.

After cooling to room temperature, 15 g (6.8 mmol) of Si{(CH$_2$)$_2$Si[(CH$_2$)$_2$SiCl$_3$]$_3$}$_4$ in 35 ml of THF were added dropwise with occasional cooling with ice in such a manner that the reaction temperature was 20 to 30° C. Stirring was then continued for a further 6 hours at room temperature; after dilution with 250 ml of hexane, the mixture was finally hydrolysed with 250 ml of saturated ammonium chloride solution, the organic phase was separated and washed three times with 200 ml portions of saturated sodium chloride solution and once with 200 ml of water. After drying over magnesium sulfate and removal of the volatile constituents by distillation, the product was obtained as a light yellow oil.

Yield: 13.2 g, corresponding to 81% of theoretical.

EXAMPLE 26

Si{(CH$_2$)$_2$Si[(CH$_2$)$_2$Si[(CH$_2$)$_3$BCl$_2$]$_3$]$_3$}$_4$

A mixture of 16 ml (11.6 g; 100.2 mmol) of triethylsilane and 6.12 g (2.54 mmol) of Si{(CH$_2$)$_2$Si[(CH$_2$)$_2$Si(C$_3$H$_5$)$_3$]$_3$}$_4$ were added dropwise to 8.5 ml (11.5 g; 97.7 mmol) of boron trichloride at −70° C. in such a manner that the temperature during the exothermic reaction did not rise above −60° C. (internal thermometer). After the dropwise addition (approx. 90 min), the reaction mixture was stirred for a further 30 minutes at −70° C., then heated to room temperature and stirred for a further 15 hours. In order to remove small quantities of pyrophoric, highly volatile constituents, argon was then passed through the solution for 2 hours (passage through dilute sodium hydroxide solution). Finally, any remaining volatile constituents were removed by distillation under a vacuum, the reaction mixture slowly being heated to up to 40° C. during this operation. The product was obtained as a colourless wax.

Yield: 11.8 g, corresponding to 86% of theoretical.
$^{11}$B{$^1$H} NMR (CDCl$_3$): δ=62.2 ppm.

EXAMPLE 27

Production of Si{(CH$_2$)$_2$Si[(CH$_2$)$_2$Si[(CH$_2$)$_3$B (C$_6$F$_5$)$_3$]$_3$]$_3$}$_4$$^{36-}$36H$_3$C—(CH$_2$)$_{10}$—N(CH$_3$)$_2$H$^+$ a) 12.7 ml (20.2 mmol) of a 1.6 molar solution of n-butyllithium in hexane were added dropwise with stirring at −70° C. to 5.0 g (20.2 mmol) of bromopentafluorobenzene in 120 ml of hexane in such a manner that there was no observable rise in temperature. After a further 2 hours' stirring at this temperature, 1.0 g (0.2 mmol) of Si{(CH$_2$)$_2$Si[(CH$_2$)$_2$Si[(CH$_2$)$_3$BCl$_2$]$_3$]$_3$}$_4$ in 10 ml of toluene were finally added dropwise, then the reaction mixture was heated to room temperature within 3 hours and stirred for a further 60 hours. A colourless suspension was obtained.

b) 1.6 g (6.7 mmol) of N,N-dimethylundecylammonium hydrochloride (produced as described in b) in Example 20) in 40 ml of methylene chloride were stirred into the solution obtained in a) and stirred for 20 hours at room temperature. The volatile constituents were then removed under a vacuum and the residue extracted with 60 ml of methylene chloride. After filtration and removal of the solvent by distillation under a vacuum, the product was obtained as a light yellow wax.

Yield: 3.7 g, corresponding to 70% of theoretical.
$^{11}$B{$^1$H} NMR (CDCl$_3$): δ=−16.1 ppm.

EXAMPLE 28

Polymerization of Ethylene

The polymerization from Example 21 was repeated, with the difference that 0.5 ml of a solution of 132.6 mg of the compound from Example 27 in 4.25 ml of toluene (=0.6 μmol of Si{(CH$_2$)$_2$Si[(CH$_2$)$_2$Si[(CH$_2$)$_3$B(C$_6$F$_5$)$_3$]$_3$]$_3$}$_4$$^{36-}$36 [CH$_3$(CH$_2$)$_{10}$NH(CH$_3$)$_2$]$^+$ was used instead of the solution of the compound from Example 21. 1.6 g of polyethylene were obtained.

EXAMPLE 29

Production of Si[(CH$_2$)$_3$B(C$_4$H$_9$)$_3$]$_4$$^{4-}$4Li$^+$ 14.3 ml (22.9 mmol) of a 1.6 molar solution of n-butyllithium in hexane were diluted with 30 ml of hexane and cooled to −70° C. 5.5 g (22.9 mmol) of MPEDA were then stirred in and 1.0 g (1.9 mmol) of Si[(CH$_2$)$_3$BCl$_2$]$_4$ in 5 ml of hexane was finally added dropwise. After the exothermic reaction (up to approx. −60° C.), the reaction mixture was stirred for a further 30 minutes at −70° C. and then heated to room temperature. After 15 hours' stirring, the volatile constituents were removed by distillation under a vacuum; a white solid was obtained which was completely soluble in DMSO.

$^{11}$B{$^1$H} NMR (CDCl$_3$): δ=−16.8 ppm.

EXAMPLE 30

Production of Si[(CH$_2$)$_3$B(C$_4$H$_9$)$_3$]$_4$$^{4-}$4N(CH$_3$)$_4$$^+$ a) 14.3 ml (22.9 mmol) of a 1.6 molar solution of n-butyllithium in hexane were diluted with 30 ml of hexane and cooled to −70° C. 1.0 g (1.9 mmol) of Si[(CH$_2$)$_3$BCl$_2$]$_4$ in 5 ml of hexane was then added dropwise. After the exothermic reaction (up to approx. −60° C.), the reaction mixture was stirred for a further 30 minutes at −70° C. and finally heated to room temperature.

After 60 hours' stirring, the reaction mixture was filtered and the resultant colourless solid dried under a vacuum.

Yield: 1.8 g.
$^{11}$B{$^1$H} NMR (CDCl$_3$): δ=−16.7 ppm.

b) 0.84 g (7.6 mmol) of tetramethylammonium chloride and 40 ml of methylene chloride were added to the solid obtained according to a) and the reaction mixture was stirred for 60 hours at room temperature. After filtration and removal of the volatile constituents by distillation, the product was obtained from the mother liquor as a colourless solid.

Yield: 1.4 g, corresponding to 59% of theoretical.
$^{11}$B{$^1$H} NMR (CDCl$_3$): δ=−16.7 ppm.

EXAMPLE 31

Production of Si[(CH$_2$)$_3$B(CH$_2$—Si (CH$_3$)$_3$)$_3$]$_4$$^{4-}$4Li$^+$ 22.9 ml (22.9 mmol) of a 1.0 molar solution of trimethylsilylmethyllithium in hexane were diluted with 60 ml of hexane and cooled to −70° C. 5.5 g (22.9 mmol) of MPEDA were then stirred in and 1.0 g (1.9 mmol) of Si[(CH$_2$)$_3$BCl$_2$]$_4$ in 5 ml of hexane was finally added dropwise. The reaction mixture was then stirred for 30 minutes at −70° C. and then heated to room temperature. After 15 hours' stirring, the volatile constituents were removed by distillation under a vacuum; a white solid was obtained, which was completely soluble in DMSO.

$^{11}$B{$^1$H} NMR (CDCl$_3$): δ=−1.8 ppm (wide).

EXAMPLE 32

Production of Si{(CH$_2$)$_2$Si[(CH$_2$)$_3$B(n-C$_4$H$_9$)$_3$]$_3$}$_4$$^{12-}$12Li$^+$ 12.9 ml (20.7 mmol) of a 1.6 molar solution of n-butyllithium in hexane were diluted with 30 ml of hexane and cooled to −70° C. 4.9 g (20.7 mmol) of MPEDA were then stirred in and 1.0 g (0.57 mmol) of Si{(CH$_2$)$_2$Si[(CH$_2$)$_3$BCl$_2$]$_3$}$_4$ in 5ml of hexane was finally added dropwise. The reaction mixture was then stirred for 30 minutes at −70° C. and then heated to room temperature. After 15 hours' stirring, the volatile constituents were removed by distillation under a vacuum; a white solid was obtained, which was completely soluble in DMSO.

$^{11}$B{$^1$H} NMR (CDCl$_3$): δ=−15.9 ppm.

EXAMPLE 33

Production of Si{(CH$_2$)$_2$Si[(CH$_2$)$_3$B(sec.-C$_4$H$_9$)$_3$]$_3$}$_4$$^{12-}$12Li$^+$ 15.9 ml (20.7 mmol) of a 1.3 molar solution of sec.-butyllithium in cyclohexane were diluted with 30 ml of hexane and cooled to −70° C. 4.9 g (20.7 mmol) of MPEDA were then stirred in and 1.0 g (0.57 mmol) of Si{(CH$_2$)$_2$Si[(CH$_2$)$_3$BCl$_2$]$_3$}$_4$ in 5 ml of hexane was finally added dropwise. After the exothermic reaction (up to −60° C.), the reaction mixture was then stirred for 30 minutes at −70° C. and then heated to room temperature. After 15 hours' stirring, the volatile constituents were removed by distillation under a vacuum; a white solid was obtained, which was completely soluble in DMSO.

$^{11}$B{$^1$H} NMR (CDCl$_3$): δ=−13.7 ppm and −14.9 ppm.

EXAMPLE 34

Production of Si{(CH$_2$)$_2$Si[(CH$_2$)$_3$B(CH$_2$—C(CH$_3$)$_3$)$_3$]$_3$}$_4$$^{12-}$12Li$^+$ (Neopentyllithium was produced according to *J. Am. Chem. Soc.* 1959, 81, 1617 from neopentyl chloride and lithium powder; content was determined by double titration according to *J. Am. Chem. Soc.* 1944, 66, 1515).

23.0 ml (23.0 mmol) of a 1.0 molar solution of neopentyllithium in diethyl ether were diluted with 30 ml of hexane and cooled to −70° C. 1.0 g (0.57 mmol) of Si{(CH$_2$)$_2$Si[(CH$_2$)$_3$BCl$_2$]$_3$}$_4$ in 5 ml of hexane was then added dropwise with stirring and the reaction mixture was then stirred for 30 minutes at −70° C. and the heated to room temperature. After 15 hours' stirring, the volatile constituents were removed by distillation under a vacuum; a white solid was obtained, which was completely soluble in DMSO.

$^{11}$B{$^1$H} NMR (CDCl$_3$): δ=−14.7 ppm.

EXAMPLE 35

Production of Si{(CH$_2$)$_2$Si[(CH$_2$)$_3$B(C$_6$H$_5$)$_3$]$_3$}$_4$$^{12-}$12Li$^+$ 12.7 ml (23.0 mmol) of a 1.8 molar solution of phenyllithium in cyclohexane/diethyl ether (70:30) were diluted with 30 ml of hexane and cooled to −70° C. 1.0 g (0.57mmol) of Si{(CH$_2$)$_2$Si[(CH$_2$)$_3$BCl$_2$]$_3$}$_4$ in 5 ml of hexane was then added dropwise with stirring and the reaction mixture was then stirred for 30 minutes at −70° C. and then heated to room temperature. After 15 hours' stirring, the volatile constituents were removed by distillation under a vacuum; a white solid was obtained, which was completely soluble in DMSO.

$^{11}$B{$^1$H} NMR (CDCl$_3$): δ=−9.8 ppm.

EXAMPLE 36

Production of Si{(CH$_2$)$_2$Si[(CH$_2$)$_3$B(C$_6$H$_5$)$_3$]$_3$}$_4$$^{12-}$12N(CH$_3$)$_4$$^+$ a) 12.7 ml (23.0 mmol) of a 1.8 molar solution of phenyllithium in cyclohexane/diethyl ether (70:30) were diluted with 30 ml of hexane and cooled to −70° C. 1.0 g (0.57 mmol) of Si{(CH$_2$)$_2$Si[(CH$_2$)$_3$BCl$_2$]$_3$}$_4$ in 5 ml of hexane was then added dropwise with stirring and the reaction mixture was then stirred for 30 minutes at −70° C. and then heated to room temperature.

After 15 hours' stirring, the volatile constituents were removed by distillation under a vacuum; a white solid was obtained, which was completely soluble in DMSO.

$^{11}$B{$^1$H} NMR (CDCl$_3$): δ=−9.9 ppm.

b) The solid obtained according to a) was suspended in 50 ml of methylene chloride and cooled to −70° C. 0.66 g (6.9 mmol) of trimethylammonium chloride were then stirred in, the reaction mixture was heated to room temperature and stirred for a further 15 hours. After filtration through diatomaceous earth, volatile constituents were removed from the resultant clear mother liquor under a vacuum; the product was obtained as a light yellow wax.

$^{11}$B{$^1$H} NMR (CDCl$_3$): δ=−9.8 ppm.

EXAMPLE 37

Production of Si{(CH$_2$)$_2$Si[(CH$_2$)$_3$B(C$_6$H$_5$)$_3$]$_3$}$_4$$^{12-}$12C$_6$H$_5$—(CH$_3$)$_2$H$^+$ a) 12.7 ml (23.0 mmol) of a 1.8 molar solution of phenyllithium in cyclohexane/diethyl ether (70:30) were diluted with 30 ml of hexane and cooled to −70° C. 1.0 g (0.57 mmol) of Si{(CH$_2$)$_2$Si[(CH$_2$)$_3$BCl$_2$]$_3$}$_4$ in 5 ml of hexane was then added dropwise with stirring and the reaction mixture was then stirred for 30 minutes at −70° C. and then heated to room temperature.

After 15 hours' stirring, the volatile constituents were removed by distillation under a vacuum.

b) The solid obtained according to a) was suspended in 100 ml of methylene chloride and cooled to −70° C. 1.1 g (6.0 mmol) of dimethylanilinium chloride were then stirred in and stirred for 30 minutes at −70° C. The reaction mixture was then heated to room temperature and stirred for a further 15 hours. After filtration through diatomaceous earth, volatile constituents were removed from the resultant clear mother liquor under a vacuum; the product was obtained as a light yellow wax.

$^{11}$B{$^1$H} NMR (CDCl$_3$): δ=−9.8 ppm.

EXAMPLE 38

Production of $Si[(CH_2)_3BF_2]_4$

At 0° C., 6.53 g (28.7 mmol) of antimony trifluoride were stirred into 5 g (9.6 mmol) of $Si[(CH_2)_3BCl_2]_4$ in 70 ml of hexane. After 1 hour at 0° C., the white suspension was heated to room temperature and stirred overnight. The precipitate was then filtered off and the volatile constituents removed by distillation under a vacuum. During the vacuum distillation, a small quantity of a colourless precipitate again precipitated; in order to separate this precipitate, 30 ml of hexane were added to the resultant.residue and the mixture kept overnight at 4° C. Filtration was then repeated and, once the solvent had been removed by distillation under a vacuum, the product was obtained as a colourless oil.

$C_{12}H_{24}B_4F_8Si$, M=391.647 g/mol; $^1H$ NMR ($CD_2Cl_2$): δ=0.63 ppm (m, 2H, Si—$CH_2$), 1.12 ppm (m, 2H, $CH_2$—$CH_2$—$CH_2$), 1.50 ppm (m, 2H, B—$CH_2$); $^{13}C\{^1H\}$ NMR: δ=16.8 ppm (Si—$CH_2$), 18.1 ppm (signals of Si—$CH_2$—$CH_2$ and B—$CH_2$ superimposed); $^{19}F\{^1H\}$ NMR: δ=−77.0 ppm, $^{11}B\{^1H\}$ NMR: δ=28.9 ppm.

What is claimed is:

1. A dendrimeric compound of general formula

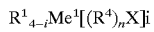
(I), wherein

X represents $Me^2R^2R^3(R^y)_r$, $R^1$, $R^2$, $R^3$, $R^y$ are identical or different, can optionally be singly- or multiply-substituted, and represent hydrogen, $C_5$–$C_{20}$ cycloalkyl, $C_1$–$C_{20}$ alkyl, $C_7$–$C_{40}$ aralkyl, $C_6$–$C_{40}$ aryl, $C_1$–$C_{10}$ alkoxy, $C_6$–$C_{40}$ aryloxy, silyloxy or halogen, $R^4$ is a alkylene, alkenylene or alkinylene radical which is optionally interrupted by one or more heteroatoms and is optionally singly- or multiple-substituted, $Me^1$ represents an element of group IVa of the periodic table of the elements (IUPAC nomenclature), $Me^2$ represents an element of group IIIa of the periodic table of the elements (IUPAC nomenclature), i denotes an integer from 2 to 4, n represents an integer from 1 to 20, and r can be 0 or 1, wherein when r=1 the $Me^2$ radical carries a negative formal charge and if there is a negative formal charge on $Me^2$ this is compensated for by a cation, or wherein X represents $Me^1R^5_a[(R^4)_mMe^2R^2R^3 (R^y)_r]_{3-a}$, $Me^1$, $Me^2$, $R^1$, $R^2$, $R^3$, $R^4$, $R^y$, i, n and r have the aforementioned meanings $R^5$ has the same meaning as the $R^1$, $R^2$, $R^3$ and $R^y$ radicals, m is identical to or different from n and represents integers from 1 to 20, and a denotes 0, 1 or 2, or wherein X represents $Me^1R^5_a[(R^4)_mMe^1R^6_b[(R^4)_pMe^2R^2R^3 (R^y)_r]_{3-b}]_{3-a}$, $Me^1$, $Me^2$, $R^1$, $R^2$, $R^3$, $R^4$, $R^y$, i, n, r, m and a have the aforementioned meanings $R^6$ has the same meaning as the $R^1$, $R^2$, $R^3$, $R^y$ and $R^5$ radicals, b represents 0, 1 or 2, and p represents integers from 1 to 20, wherein said which compounds are produced by the reaction of silicon tetrachloride in a Grignard reaction to form tetraallylsilane, which is subsequently reacted several times alternately a) with trichlorosilane in a quantitative reaction in the presence of a catalyst, and subsequently b) with an allyl compound in a Grignard reaction, using a suitable solvent each time, until a dendrimeric skeletal structure comprising outwardly pointing allyl groups is obtained, the outer allyl groups of which c) are converted into derivatives in a hydroboronation reaction with 9-borabicyclo[3,3,1]nonane.

wherein the following said compounds are excluded:

(1)

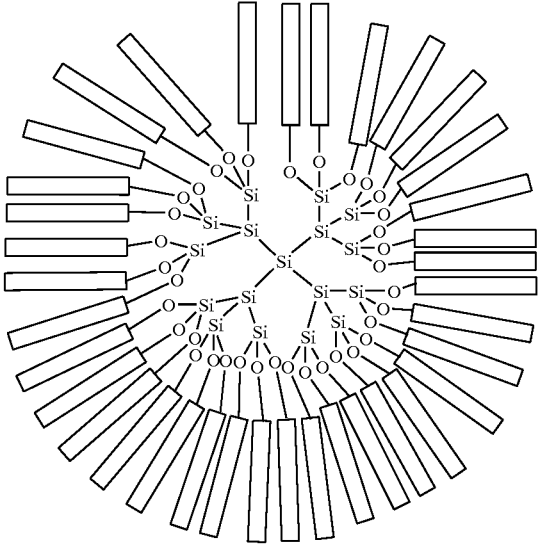

in which the rectangles represent a mesogenic group, said mesogenic groups comprising:

a) a structure of the general formula

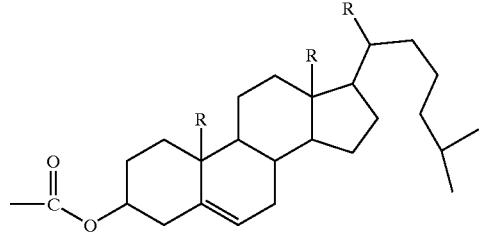

wherein R=$C_1$ to $C_6$-alkyl which might be bound to the dendrimer via a $C_3$–$C_6$-alkyl-spacer b) a mesogenic substituent of the generic formula

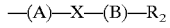

wherein $R_2$ represents an alkyl, alkoxy or, alkanoyloxy with up to 12 C-atoms in which 1 or 2 not adjacent $CH_2$ groups can be replaced by -O— or —CH=CH—, or cyano, nitro, halogen, or trifluoromethyl X represents a carbonyl —C—C— single bond, thioester group, methyleneoxy group, methylene thio group or ethylene group one of A/B represents a ring or ring system which is not aromatic or only partially aromatic, the other one being the same or having a homoaromatic or heteroaromatic structure moiety and at least one of A or B being a trans-4'-cyclohexylphenyl-system or a trans-4-trans-4'-bicyclohexyl-system or 4,4'-phenylene which can have up to 3 fluorine substituents;

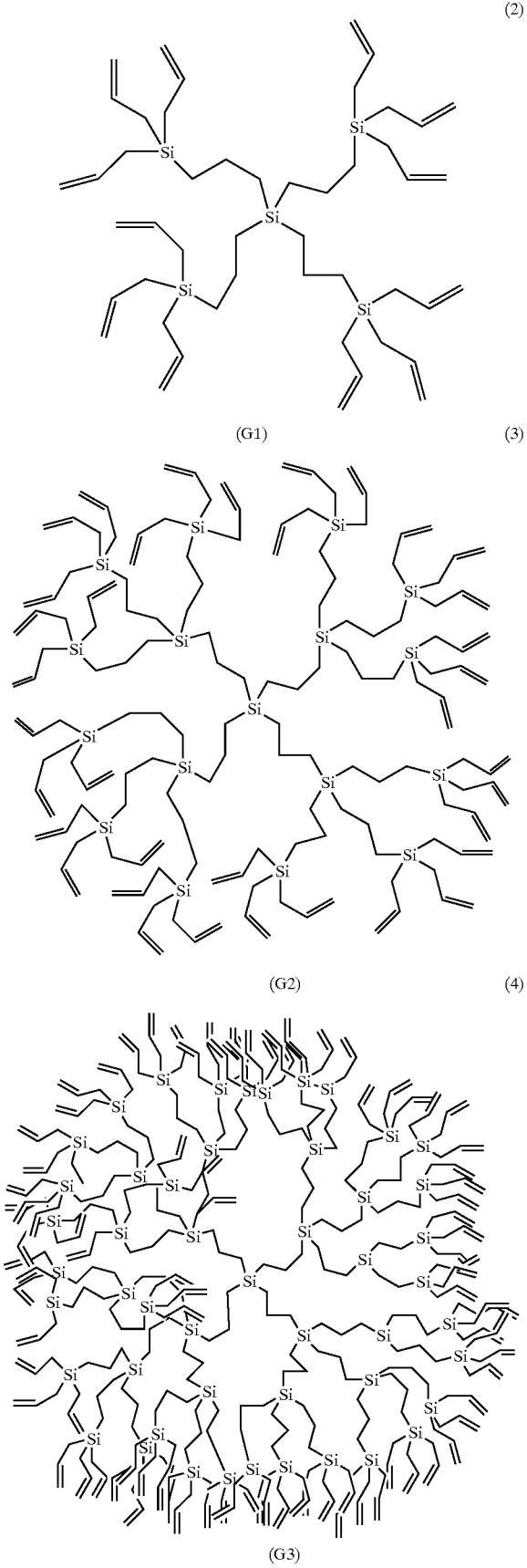

(G1) (G2) (G3)

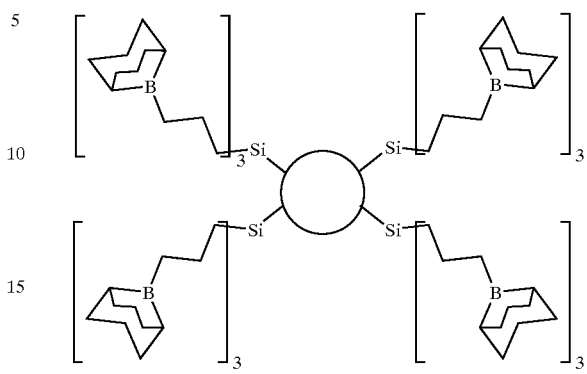

wherein said circle represents the structure G1.

2. A method of producing a new dendrimeric compound of general formula $$R^1_{4-i}Me^1[(R^4)_nX]i \qquad (I),$$

wherein

X represents $Me^2R^2R^3(R^y)_r$, $R^1$, $R^2$, $R^3$, $R^y$ are identical or different, can optionally be singly- or multiply-substituted, and represent hydrogen, $C_5$–$C_{20}$ cycloalkyl, $C_1$–$C_{20}$ alkyl, $C_7$–$C_{40}$ aralkyl, $C_6$–$C_{40}$ aryl, $C_1$–$C_{10}$ alkoxy, $C_6$–$C_{40}$ aryloxy, silyloxy or halogen, $R^4$ is a alkylene, alkenylene or alkinylene radical which is optionally interrupted by one or more heteroatoms and is optionally singly- or multiple-substituted, $Me^1$ represents an element of group IVa of the periodic table of the elements (IUPAC nomenclature), $Me^2$ represents an element of group IIIa of the periodic table of the elements (IUPAC nomenclature), i denotes an integer from 2 to 4, n represents an integer from 1 to 20, and r can be 0 or 1, wherein when r=1 the $Me^2$ radical carries a negative formal charge and if there is a negative formal charge on $Me^2$ this is compensated for by a cation, or wherein X represents $Me^1R^5_a[(R^4)_mMe^2R^2R^3(R^y)_r]_{3-a}$, $Me^1$, $Me^2$, $R^1$, $R^2$, $R^3$, $R^4$, $R^y$, i, n and r have the aforementioned meanings $R^5$ has the same meaning as the $R^1$, $R^2$, $R^3$ and $R^y$ radicals, m is identical to or different from n and represents integers from 1 to 20, and a denotes 0, 1 or 2, or wherein X represents $Me^1R^5_a[(R^4)_mMe^1R^6_b[(R^4)_pMe^2R^2R^3(R^y)_r]_{3-b}]_{3-a}$, $Me^1$, $Me^2$, $R^1$, $R^2$, $R^3$, $R^4$, $R^y$, i, n, r, m and a have the aforementioned meanings $R^6$ has the same meaning as the $R^1$, $R^2$, $R^3$, $R^y$ and $R^5$ radicals, b represents 0, 1 or 2, and p represents integers from 1 to 20, wherein said compounds are produced by the reaction of silicon tetrachloride in a Grignard reaction to form tetraallylsilane, which is subsequently reacted several times alternately
a) with trichlorosilane in a quantitative reaction in the presence of a catalyst, and subsequently
b) with an allyl compound in a Grignard reaction, using a suitable solvent each time, until a dendrimeric skeletal structure comprising outwardly pointing allyl groups is obtained, the outer allyl groups of which
c) are converted into derivatives in a hydroboronation reaction with 9-borabicyclo[3,3,1]nonane.

wherein the following said compounds are excluded:

(1)

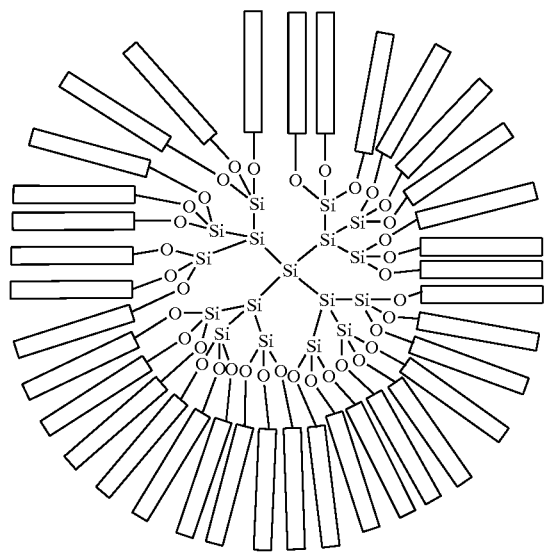

in which the rectangles represent a mesogenic group, said mesogenic groups comprising:
a) a structure of the general formula

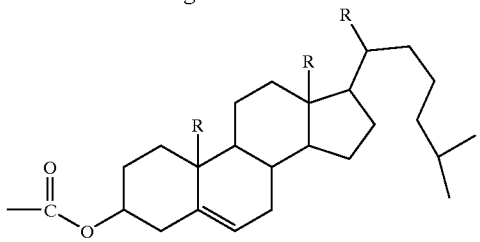

wherein R=C$_1$ to C$_6$-alkyl
which might be bound to the dendrimer via a C$_3$–C$_6$-alkyl-spacer
b) a mesogenic substituent of the generic formula

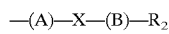
—(A)—X—(B)—R$_2$ wherein
R$_2$ represents an alkyl, alkoxy or, alkanoyloxy with up to 12 C-atoms in which 1 or 2 not adjacent CH$_2$ groups can be replaced by —O— or —CH=CH—, or cyano, nitro, halogen, or trifluoromethyl
X represents a carbonyl —C—C— single bond, thioester group, methyleneoxy group, methylene thio group or ethylene group one of A/B represents a ring or ring system which is not aromatic or only partially aromatic, the other one being the same or having a homoaromatic or heteroaromatic structure moiety and at least one of A or B being a trans4'-cyclohexylphenyl-system or a trans-4-trans4'-bicyclohexyl-system or 4,4'-phenylene which can have up to 3 fluorine substituents;

(2)

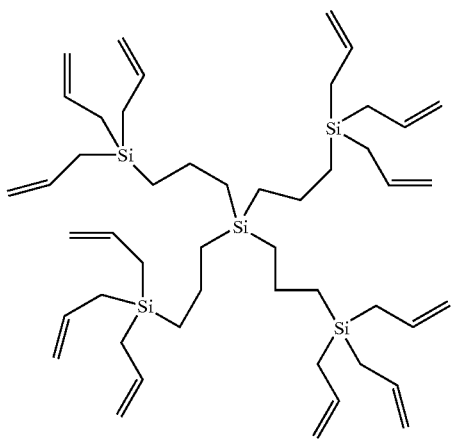
(G1)

(3)

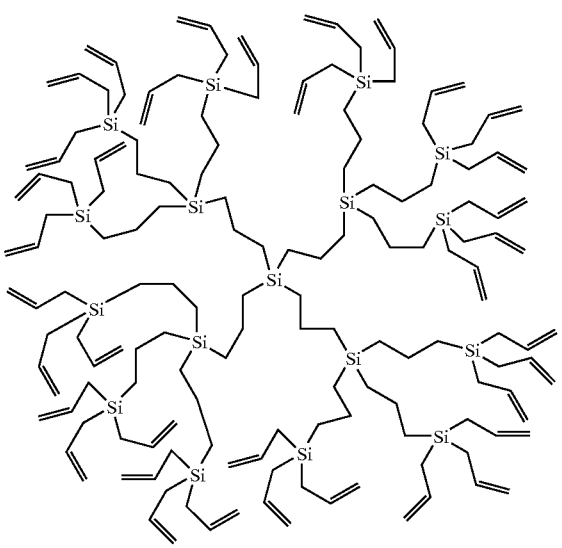
(G2)

(4)

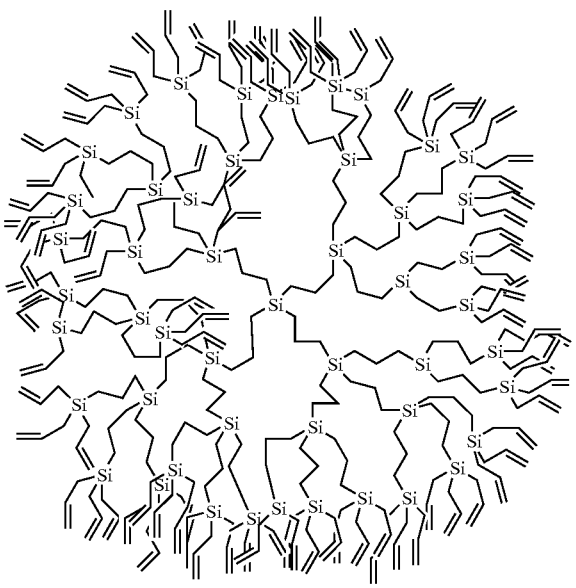
(G3)
and

-continued (5)

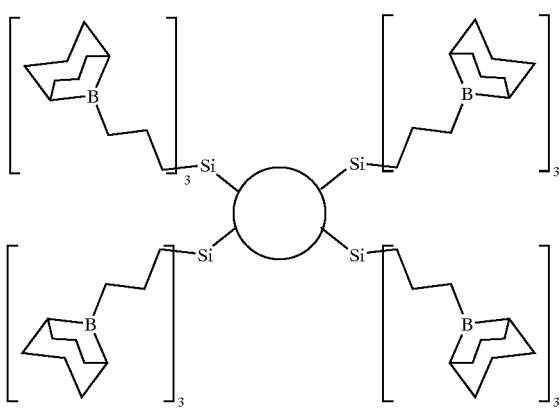

wherein said circle represents the structure G1,
wherein said compounds of general formula (IV)

$$R^1_{4-i}Me^1[(R^7)_{n-2}Y]_i \quad (IV),$$

wherein
  Y represents $CR^8{=}CR^9R^{10}$,
  $R^8$, $R^9$ and $R^{10}$ are identical or different and represent hydrogen, alkyl, aryl or halogen,
  $R^7$ has the same meaning as the $R^4$ radicals in formula (I);
  n represents an integer from 2 to 20, and
or wherein
  Y represents $Me^1R^5_a[(R^7)_{m-2}(CR^8{=}CR^9R^{10})]_{3-a}$, or wherein
  Y represents $Me^1R^5_a[(R^4)_m Me^1R^6_b[(R^7)_{p-2}(CR^8{=}CR^9R^{10})]_{3-b}]_{3-a}$,
  m, p represent integers from 2 to 20, and wherein all the radicals cited in the formulae for Y have the aforementioned meanings,
are reacted with compounds of general formula (V)

$$R^{11}{-}Me^2R^2R^3 \quad (V),$$

wherein
  $R^{11}$ represents hydrogen or $C_1$–$C_{30}$ alkyl,
and if r=1, the product obtained therefrom is reacted further with compounds of general formula (VI)

$$Me^3{-}R^y \quad (VI),$$

wherein
  $Me^3$ is an alkali metal and $R^y$ has the meaning given above,
or are reacted with compounds of general formula (VII)

$$Hal_q{-}Me^4{-}R^y_{2-q} \quad (VII),$$

wherein
  $Me^4$ is an alkaline earth metal or a transition metal of the 1st or 2nd subgroup,
  Hal represents halogen,
  q is 0 or 1.

* * * * *